United States Patent
Lee et al.

(10) Patent No.: US 12,368,832 B2
(45) Date of Patent: Jul. 22, 2025

(54) DATA PROCESSING DEVICE AND DATA PROCESSING METHOD

(71) Applicant: MEDIT CORP., Seoul (KR)

(72) Inventors: Dong Hoon Lee, Seoul (KR); Myoung Woo Song, Seoul (KR)

(73) Assignee: MEDIT CORP., Seoul (KR)

( * ) Notice: Subject to any disclaimer, the term of this patent is extended or adjusted under 35 U.S.C. 154(b) by 1 day.

(21) Appl. No.: 18/278,684

(22) PCT Filed: Feb. 23, 2022

(86) PCT No.: PCT/KR2022/002642
§ 371 (c)(1),
(2) Date: Aug. 24, 2023

(87) PCT Pub. No.: WO2022/182121
PCT Pub. Date: Sep. 1, 2022

(65) Prior Publication Data
US 2024/0129447 A1    Apr. 18, 2024

(30) Foreign Application Priority Data

Feb. 26, 2021  (KR) ........................ 10-2021-0026716
Jan. 6, 2022   (KR) ........................ 10-2022-0002285

(51) Int. Cl.
*H04N 13/211*    (2018.01)
*A61C 9/00*      (2006.01)
(Continued)

(52) U.S. Cl.
CPC ......... *H04N 13/211* (2018.05); *H04N 13/117* (2018.05); *H04N 13/30* (2018.05); *A61C 9/0053* (2013.01)

(58) Field of Classification Search
CPC ....... A61B 5/00; A61B 5/0037; A61B 5/0088; A61B 5/4547; A61B 5/7425;
(Continued)

(56) References Cited

U.S. PATENT DOCUMENTS 10,108,269 B2  10/2018  Sabina et al.
RE48,221 E      9/2020  Ojelund et al.
(Continued)

FOREIGN PATENT DOCUMENTS

JP   2019-140601 A   8/2019
JP   2021-007608 A1  1/2021
(Continued)

OTHER PUBLICATIONS

International Search Report for PCT/KR2022/002642 dated Jun. 9, 2022 (PCT/ISA/210).

*Primary Examiner* — Christopher S Kelley
*Assistant Examiner* — Ana Picon-Feliciano
(74) *Attorney, Agent, or Firm* — Sughrue Mion, PLLC

(57) ABSTRACT

There is provided a data processing method including displaying three-dimensional scan data, and changing display of the three-dimensional scan data in response to a remote control signal received from a scanner, wherein the remote control signal includes a signal for controlling a virtual camera obtaining an image of the three-dimensional scan data.

13 Claims, 24 Drawing Sheets

(51) Int. Cl.
*H04N 13/117* (2018.01)
*H04N 13/30* (2018.01)

(58) Field of Classification Search
CPC ....... A61C 9/0053; A61C 9/006; G06T 15/20;
G06T 17/00; G06T 2210/41; G16H
30/20; G16H 30/40; G16H 50/50; H04N
13/117; H04N 13/211; H04N 13/30;
H04N 7/183
USPC .......................................................... 348/66
See application file for complete search history.

(56) References Cited

U.S. PATENT DOCUMENTS

| | | | |
|---|---|---|---|
| 2013/0257718 A1* | 10/2013 | Ojelund | G06F 3/011 |
| | | | 345/156 |
| 2014/0226885 A1 | 8/2014 | Keating et al. | |
| 2017/0289523 A1* | 10/2017 | Lee | H04N 13/207 |
| 2017/0295320 A1 | 10/2017 | Lee | |
| 2020/0022788 A1 | 1/2020 | Hansen | |

FOREIGN PATENT DOCUMENTS

| | | |
|---|---|---|
| KR | 10-1596566 B1 | 2/2016 |
| KR | 10-1788039 B1 | 10/2017 |
| KR | 10-1977181 B1 | 5/2019 |
| KR | 10-2020-0115580 A | 10/2020 |
| WO | 2019/147984 A1 | 8/2019 |

\* cited by examiner

DATA PROCESSING DEVICE AND DATA PROCESSING METHOD

CROSS REFERENCE TO RELATED APPLICATIONS

This application is a National Stage of International Application No. PCT/KR2022/002642 filed Feb. 23, 2022, claiming priorities based on Korean Patent Application No. 10-2021-0026716 filed Feb. 26, 2021 and on Korean Patent Application No. 10-2022-0002285 filed Jan. 6, 2022.

TECHNICAL FIELD

Various embodiments relate to a data processing device and a data processing method, and more particularly, to a data processing device remotely controlled according to a control command from a scanner and an operating method thereof.

BACKGROUND ART

A scanner may obtain two-dimensional scan data by scanning an object. A data processing device such as a personal computer (PC) connected to the scanner may generate a three-dimensional virtual model by using the two-dimensional scan data obtained by the scanner and output the three-dimensional virtual model on a screen.

A user may need to manipulate the data processing device while scanning. For example, a user may want to change options or settings related to scanning, change a scanning operation, or check whether a three-dimensional virtual model is successfully created. In this case, the user may operate the data processing device to execute a corresponding function.

However, because the scanner and the data processing device are often physically separated from each other, it is difficult for a user to manipulate the data processing device located away from the scanner while performing a scanning operation by using the scanner. In addition, it is difficult for a user to check scan data in detail in real time through a screen of a data processing device located away from the user while performing a scan operation. In addition, in an environment where hygiene is important, such as when the object is a patient's oral cavity, there is a problem in that it is not sanitary to operate the data processing device while scanning the oral cavity.

DESCRIPTION OF EMBODIMENTS

Technical Problem

Various embodiments provide a data processing device remotely controlled according to a control command from a scanner and a data processing method.

Various embodiments are intended to provide a data processing device and data processing method for changing the display of three-dimensional scan data in response to a control command from a scanner.

Solution to Problem

A data processing method performed by a data processing device according to an embodiment includes displaying three-dimensional scan data, and changing display of the three-dimensional scan data in response to a remote control signal received from a scanner, wherein the remote control signal includes a signal for controlling a virtual camera obtaining an image of the three-dimensional scan data.

MODE OF DISCLOSURE

Figure 1:
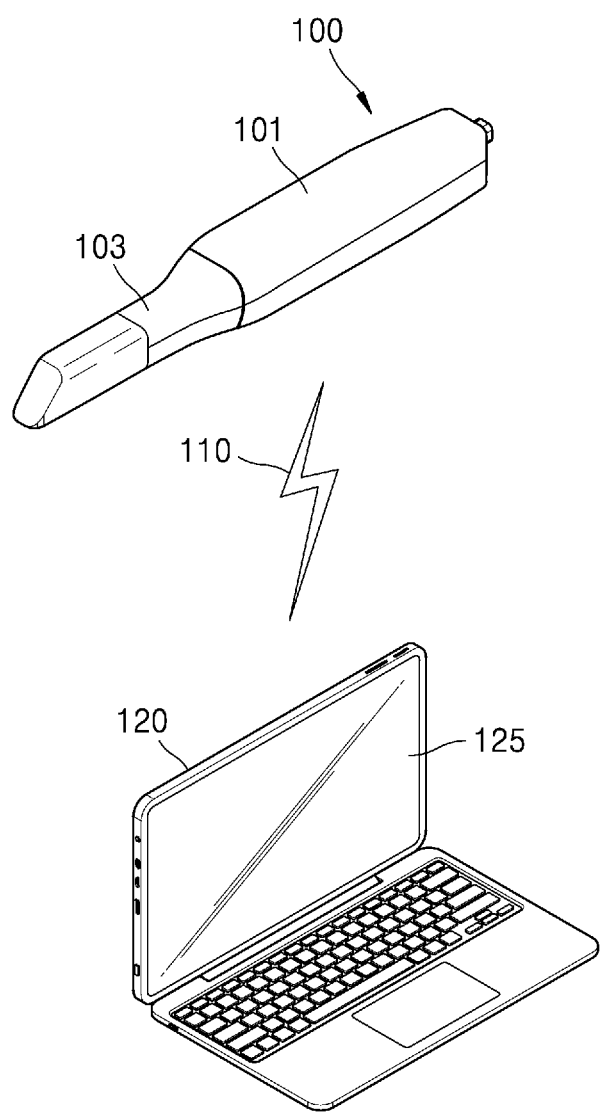
FIG. 1 is a diagram for explaining a data processing system according to an embodiment.

In an embodiment, the remote control signal may further include a signal instructing to output a remote control mode screen.

In an embodiment, the data processing method may further include outputting a remote scanning screen in response to receiving a scan start signal from the scanner.

In an embodiment, the remote scanning screen may include the three-dimensional scan data and a live view image, and the live view image may be a two-dimensional image of an object obtained by the scanner.

In an embodiment, the data processing method may further include receiving the remote control signal from the scanner, wherein the receiving of the remote control signal from the scanner may include receiving, as the remote control signal, a user input signal for selecting a control button provided in the scanner.

In embodiment, the remote control mode screen may be different from a basic mode screen in at least one of a coordinate system, an output data type, and an output data size.

In an embodiment, the data processing method may further include receiving a signal instructing to output a basic mode screen, wherein the receiving of the signal instructing to output the basic mode screen may include at least one of receiving a user input signal for selecting to output a basic mode screen among menus output on the remote control mode screen through a control button provided in the scanner, while outputting the remote control mode screen, and sensing an input signal by an input unit of a data processing device.

In an embodiment, the data processing method may further include outputting a remote scan operation selection screen in response to receiving a user input signal by long pressing a scan button provided in the scanner from the scanner, and changing a scan operation according to a user input signal through a control button provided in the scanner, wherein the changing of the scan operation may include completing data generated in a previous scan operation.

In an embodiment, the data processing method may further include outputting a remote scan data view screen in response to receiving a scan end signal from the scanner.

In an embodiment, the data processing method may further include receiving, from the scanner, a user input signal for selecting a control type for the three-dimensional scan data included in the remote scan data view screen, wherein the control type for the three-dimensional scan data may include at least one of movement, rotation, and size change of the three-dimensional scan data.

In an embodiment, the signal for controlling the virtual camera may include a selected control type and a signal according to an input of a control button provided in the scanner, wherein the changing of the display of the three-dimensional scan data may include outputting an image obtained by photographing the three-dimensional scan data with the virtual camera controlled according to a signal for controlling the virtual camera.

A data processing device according to an embodiment includes a display, a communication unit configured to transmit and receive information to and from a scanner, and a processor configured to execute one or more instructions, wherein the processor is further configured to execute the one or more instructions to display three-dimensional scan data through the display, and change the display of the three-dimensional scan data in response to a remote control signal received from the scanner, and the remote control signal includes a signal for controlling a virtual camera obtaining an image of the three-dimensional scan data.

A scanner according to an embodiment includes a communication unit configured to transmit and receive information to and from a data processing device, a user input unit, and a processor configured to execute one or more instructions, wherein the processor is further configured to execute the one or more instructions to transmit a remote control signal corresponding to a user input input through the user input unit to the data processing device, and control the data processing device to change display of three-dimensional scan data.

The present specification describes the principle of the disclosure and discloses embodiments to clarify the scope of rights of the disclosure and enable one skilled in the art to which the disclosure pertains to work the disclosure. The disclosed embodiments may be implemented in various forms.

Throughout the specification, like reference numerals denote like constituent elements. The present specification does not describe all elements of embodiments, and general matters in the technical field to which the disclosure pertains, or redundant descriptions between embodiments, are omitted. Terms such as "part" or "portion" used in the specification may be embodied by software or hardware, and according to embodiments, a plurality of "parts" or "portions" may be embodied as one unit or elements or one "part" or "portion" may include a plurality of units or elements. Hereinafter, the operation principle and embodiments of the disclosure are described with reference to the accompanying drawings.

In the present specification, an object is a subject to be photographed and may include a part of a body or a model of the part of the body. For example, an object may include various body parts, such as an ear, nose, oral cavity of a human or animal, or models thereof.

In the present specification, an image may include an image that represents an object. In the present specification, an image may include an image (hereinafter, referred to as the "intraoral image") representing at least one tooth, an oral cavity including at least one tooth, or an oral cavity plaster model.

In addition, in the present specification, an intraoral image may be a two-dimensional image of an object or a three-dimensional intraoral image that represents an object in three-dimensions. As a three-dimensional intraoral image may be generated by three-dimensionally modeling a structure of an oral cavity, based on raw data, the three-dimensional intraoral image may be referred to as a three-dimensional oral cavity model. In addition, a three-dimensional oral cavity model may be referred to as a three-dimensional scan model or three-dimensional scan data. Hereinafter, in the present specification, an intraoral image is used to collectively mean a model or image two-dimensionally or three-dimensionally representing an oral cavity.

However, in the present specification, an image is not limited to an intraoral image, and may include an image of various objects, such as an ear or a nose, according to the type and body part of an object.

In addition, in the present specification, data may mean information needed to express an object in two-dimensions or three-dimensions, for example, raw data obtained by using at least one camera.

In detail, raw data is data obtained to generate an image, that is, data (for example, two-dimensional data) obtained from at least one image sensor included in a three-dimensional scanner when an object is scanned by using a three-dimensional scanner. Raw data obtained from a three-dimensional scanner may be referred to as two-dimensional image data. Raw data may mean two-dimensional images of different viewpoints obtained by a plurality of cameras when an object is scanned by using a three-dimensional scanner.

In the above, it has been described that raw data is a two-dimensional image, but is not limited thereto, and raw data may be three-dimensional image data.

It is difficult for a user to operate a data processing device located away from the scanner while performing a scan operation using a scanner, or to check data output from the data processing device in real time while performing a scan operation. In addition, when the scanner is a handheld scanner, because the handheld scanner may be inserted into the oral cavity, ear, nose, etc., it is not hygienic for the user to operate the data processing device while scanning an object by using the handheld scanner.

Disclosed embodiments are to overcome the above problems, and to provide a data processing device and a data processing method that are remotely controlled according to a control command using a scanner.

Hereinafter, embodiments will be described in detail with reference to the drawings.

FIG. 1 is a diagram for explaining a data processing system according to an embodiment.

Referring to FIG. 1, the data processing system may include a scanner 100 and a data processing device 120 coupled to the scanner 100 through a communication network 110.

The scanner 100 may be a medical device that obtains an image of an object.

In an embodiment, the scanner 100 may be of a handheld type that allows a user to scan an object while holding the handheld scanner 100 in a hand and moving. The scanner 100 may be inserted into the ear or nose and scan the inside of the ear or nose in a non-contact manner. The scanner 100 may obtain an image of at least one of an oral cavity, an ear, a nose, an artificial structure, and a plaster model modeled after the oral cavity, the ear, the nose, or the artificial structure. Alternatively, the scanner 100 may be an intraoral scanner that obtains an intraoral image of an oral cavity including at least one tooth by being inserted into the oral cavity to scan a tooth. Hereinafter, for convenience of description, a case where the scanner 100 is an intraoral scanner is described as an example, but the disclosure is not limited thereto.

The scanner 100 may include a main body 101 and a tip 103. The main body 101 may include a light projector (not shown) that projects light and a camera (not shown) that captures and obtains an image of an object.

The tip 103 is inserted into an oral cavity and may be mounted on the main body 101 in a detachable manner. The tip 103 includes a light path changing unit to direct light projected from the main body 101 to an object and direct light received from the object to the main body 101.

The scanner 100 may obtain surface information about an object, as raw data, for imaging of at least one surface of a tooth inside an oral cavity, a gingiva, and an artificial structure (for example, an orthodontic appliance including a bracket, a wire, and the like, an implant, an artificial tooth, an orthodontic auxiliary inserted in an oral cavity, and the like) that is insertable in an oral cavity.

The scanner 100 may transmit the obtained raw data to the data processing device 120 through the communication network 110.

In an embodiment, the scanner 100 may include a communication unit that transmits and receives information to and from the data processing device 120, a user input unit, and a processor that executes one or more instructions. In an embodiment, the processor may transmit a control signal corresponding to a user input input through the user input unit to the data processing device 120 through the communication unit by executing one or more instructions and remotely control the data processing device 120 operating in a remote control mode.

In an embodiment, the user input unit included in the scanner 100 may include a scan button and a control button.

In an embodiment, the scan button may be a button for controlling a scan operation of the scanner 100. The scanner 100 may receive a user input through the scan button and start or end a scan operation in response to the user input. In addition, the scanner 100 may transmit a control signal corresponding to a user input to the scan button to the data processing device 120 to inform the data processing device 120 of the operating state of the scanner 100, and accordingly may cause the data processing device 120 to operate correspondingly.

In an embodiment, the control button may be a button for controlling the data processing device 120. The scanner 100 may receive a user input through the control button and transmit a control signal corresponding to the user input to the data processing device 120 to control the operation of the data processing device 120.

The data processing device 120 may be connected to the scanner 100 through the wired or wireless communication network 110. The data processing device 120 may be any electronic device capable of receiving raw data from the scanner 100 and generating, processing, displaying, and/or transmitting an intraoral image based on the received raw data. For example, the data processing device 120 may be a computing device, such as a smart phone, a laptop computer, a desktop computer, a personal digital assistant (PDA), or a tablet personal computer (PC), but is not limited thereto. Also, the data processing device 120 may exist in the form of a server (or server device) for processing an intraoral image.

In an embodiment, the data processing device 120 may transmit a control signal to the scanner 100 to control an operation of the scanner 100 or inform an operating state of the data processing device 120. In an embodiment, the control signal transmitted from the data processing device 120 to the scanner 100 may include a control signal for at least one of a power on/off command for the scanner 100, a scan mode change of the scanner 100, and information on whether the data processing device 120 operates in a basic mode or a remote control mode.

In an embodiment, the data processing device 120 may include a display 125, a communication unit that transmits and receives information to and from the scanner 100, and a processor that executes one or more instructions. In an embodiment, the processor may be configured to, by executing one or more instructions, receive a user input requesting operation in a remote control mode, and operate in a remote control mode, which is remotely controlled according to a control command from the scanner 100 received through the communication unit, in response to receiving the user input requesting operation in the remote control mode. In an embodiment, operating the processor in the remote control mode may include controlling the display 125 to output a remote control mode screen.

In an embodiment, a data processing method performed by the data processing device 120 may include receiving a user input requesting operation in the remote control mode, and operating in the remote control mode, which is remotely controlled according to a control command through the scanner 100, in response to receiving the user input requesting operation in the remote control mode.

In an embodiment, the operating in the remote control mode may include outputting a remote control mode screen.

In an embodiment, the user input requesting operation in the remote control mode may include at least one of a user input through a control button provided in the scanner 100 and a user input selecting the remote control mode through the data processing device 120.

In an embodiment, the data processing method may further include receiving a scan command, and the outputting of the remote control mode screen may include outputting a remote scanning screen in response to receiving the scan command.

In an embodiment, the remote scanning screen may include three-dimensional scan data and a live view image, and the live view image may include a two-dimensional image of an object obtained by the scanner 100.

In an embodiment, the data processing method may further include receiving a scan end command, and the outputting of the remote control mode screen may further include outputting a remote scan data view screen in response to receiving the scan end command.

In an embodiment, the data processing method may further include receiving a user input for selecting a control type for three-dimensional scan data included in the remote scan data view screen, and the control type for the three-dimensional scan data may include at least one of three-dimensional scan data movement, rotation, and resizing.

In an embodiment, the outputting of the remote control mode screen may further include outputting a screen on which the three-dimensional scan data is controlled, based on the selected control type and a four-directional key input of the control button provided in the scanner 100.

In an embodiment, the outputting of the screen on which the three-dimensional scan data is controlled may include outputting an image obtained by photographing the three-dimensional scan data with a virtual camera operating in response to the selected control type and the four-directional key input of the control button provided in the scanner 100.

In an embodiment, the data processing method may further include receiving a request for outputting a screen before the three-dimensional scan data is controlled, and the outputting of the remote control mode screen may further include re-outputting the remote scan data view screen, which is output corresponding to receiving the scan end command, in response to receiving the request for outputting a screen before the three-dimensional scan data is controlled.

In an embodiment, the data processing method may further include receiving a user input requesting option setting information, and the outputting of the remote control mode screen may include outputting a screen including an option setting information screen in response to receiving the user input requesting the option setting information.

In an embodiment, the option setting information screen may include a setting menu for at least one of a scan setting, a scanner setting, a data setting, and a control setting.

In an embodiment, the outputting of the remote control mode screen may include outputting a remote scan operation selection screen according to a long-pressed input to a scan button provided in the scanner 100. In addition, the data processing method may further include changing a scan operation according to a user input through a four-directional key of a control button provided in the scanner 100, and the changing of the scan operation may include completing scan data generated in the previous scan operation.

In an embodiment, the data processing method may further include operating in a basic mode based on not receiving a user input requesting operation in the remote control mode, or receiving a user input requesting operation in the basic mode from the user while operating in the remote control mode. The operating in the basic mode may include outputting a basic mode screen, and at least one of a coordinate system, a type of output data, and a size of output data may be different between the remote control mode screen and the basic mode screen.

In an embodiment, the receiving of a user input requesting operation in the basic mode may include at least one of receiving a selection to switch to a basic mode from a menu displayed on the screen, through a control button provided in the scanner 100, while operating in the remote control mode and sensing a user input signal by an input unit provided in the data processing device 120. For example, when a user manipulates a mouse, keyboard, or keypad of the data processing device 120, the data processing device 120 may recognize the user's manipulation as a control signal commanding operation in the basic mode, and accordingly be switched from the remote control mode to the basic mode and operated.

The data processing device 120 may generate a three-dimensional intraoral image or additional information by processing two-dimensional image data based on the two-dimensional image data received from the scanner 100. The data processing device 120 may display the three-dimensional intraoral image and/or the additional information through the display 125, or output or transmit the three-dimensional intraoral image and/or the additional information to an external device.

As another example, the scanner 100 may obtain raw data through an intraoral scan, process the obtained raw data to generate three-dimensional data, and transmit the three-dimensional data to the data processing device 120.

The scanner 100 may obtain three-dimensional data representing the shape of an object, using the principle of triangulation by deformation of a pattern, by projecting pattern light onto the object and scanning the object onto which the pattern light is projected.

In an embodiment, the scanner 100 may obtain three-dimensional data of an object by using a confocal method. The confocal method is a non-destructive optical imaging technique for three-dimensional surface measurement, and may obtain an optical cross-sectional image with high spatial resolution by using a pinhole structure. The scanner 100 may obtain three-dimensional data by stacking two-dimensional images obtained along an axial direction.

However, this is just an example, and the scanner 100 may obtain three-dimensional data from raw data by using various methods other than the above-described method and transmit the obtained three-dimensional data to the data processing device 120. The data processing device 120 may analyze, process, display, and/or transmit received three-dimensional data.

Figure 2:
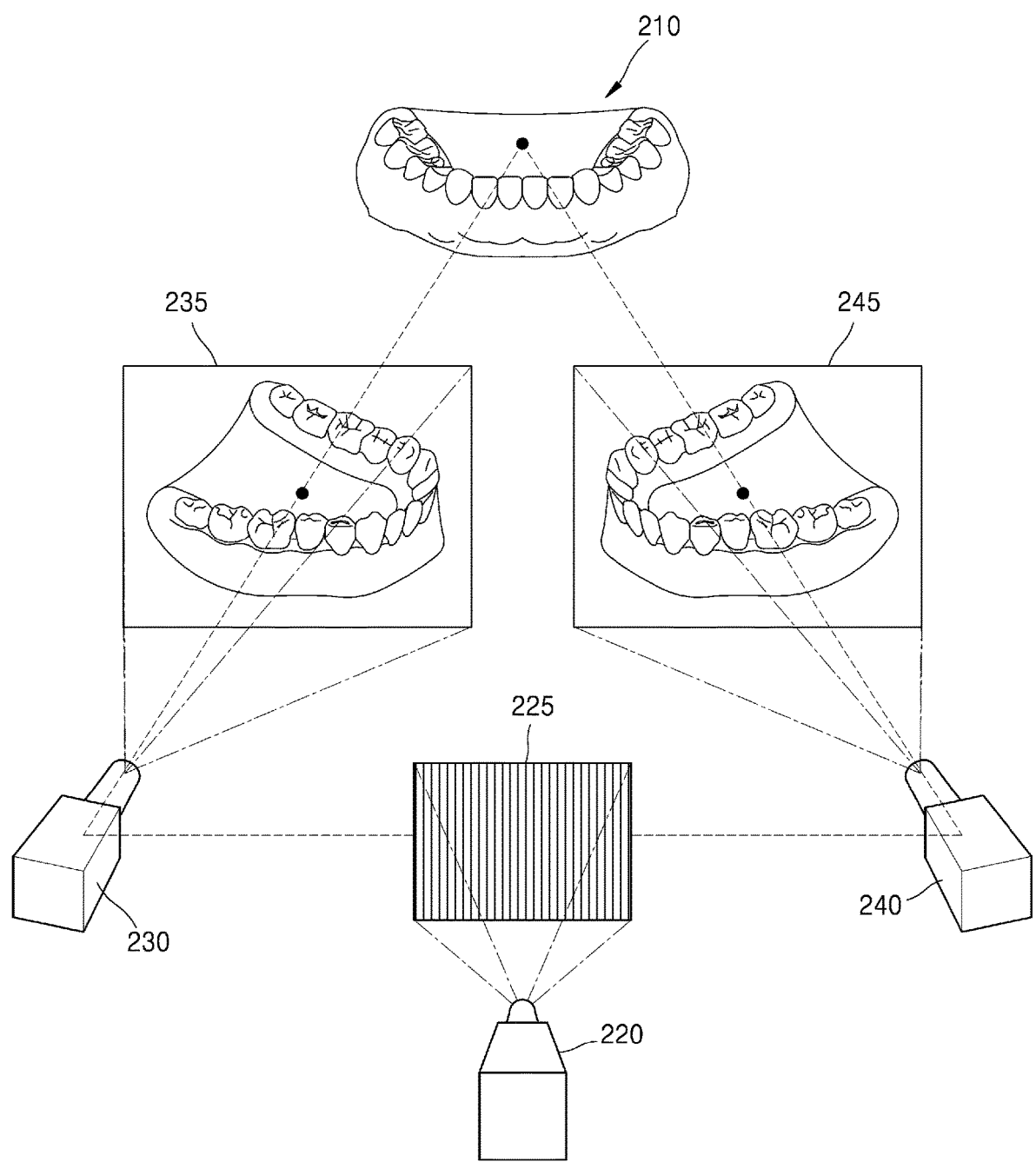
FIG. 2 is a diagram for explaining a method performed by a scanner to obtain surface data, according to an embodiment.

FIG. 2 is a diagram for explaining a method performed by a scanner to obtain surface data, according to an embodiment.

FIG. 2 is a diagram for explaining how the scanner 100 described with reference to FIG. 1 obtains three-dimensional data by imaging an object.

In an embodiment, the scanner 100 may obtain three-dimensional data of an object by using various methods. For example, the scanner 100 may obtain three-dimensional data of an object by using a confocal method. The confocal method is a method of obtaining three-dimensional information of an object based on the location of a point found through the maximum intensity of reflected light according to the refractive index of a lens through which light irradiated onto the object passes. The scanner 100 may obtain an optical cross-sectional image having high spatial resolution by using a pinhole structure. The scanner 100 may obtain three-dimensional data by stacking two-dimensional images obtained along an axial direction.

Alternatively, in another embodiment, the scanner 100 may obtain three-dimensional information of an object by using a light triangulation technique. The light triangulation technique is a technique for obtaining three-dimensional information of an object through trigonometric calculation by using a triangle formed by a light source, an object to which light emitted from the light source is irradiated, and an image sensor to which light reflected from the object is input. However, this is just an example, and the scanner 100 may obtain three-dimensional data in various ways other than the confocal method or the light triangulation method.

Hereinafter, as an example, a method in which the scanner 100 obtains three-dimensional data of an object by using light triangulation method will be described in more detail.

In an embodiment, the scanner 100 may obtain an image by using at least one camera and obtain three-dimensional data based on the obtained image.

In FIG. 2, the scanner 100 may be an optical three-dimensional scanner. The scanner 100 may use a structured light with stereo vision method to obtain three-dimensional data on the surface of an object 210.

The scanner 100 may include two or more cameras 230 and 240 and a projector 220 capable of projecting structured light 225.

The scanner 100 may project the structured light 225 to the object 210 through the projector 220, and an L camera 230 corresponding to a left field of view and an R camera 240 corresponding to a right field of view may obtain an L image 235 corresponding to the left field of view and an R image 245 corresponding to the right field of view, respectively. The L image 235 and the R image 245 may be reconstructed into three-dimensional image frames representing the surface of the object 210.

The scanner 100 may continuously obtain a two-dimensional image frame including the L image 235 and the R image 245 of the object 210. The scanner 100 or the data processing device 120 may obtain a three-dimensional image frame representing the surface shape of the object 210 from the two-dimensional image frame including the L image 235 and the R image 245. In FIG. 2, it has been illustrated that the scanner 100 obtains three-dimensional data from two images obtained using two cameras 230 and 240. However, this is just an example, and the scanner 100 may obtain an image by using only one of the two cameras 230 and 240.

The scanner 100 may obtain a plurality of two-dimensional frames by scanning the periphery of the object 210 at regular time intervals (e.g., about 10 frames to about 30 frames per second). The scanner 100 or the data processing device 120 may obtain a plurality of three-dimensional image frames from a plurality of two-dimensional image frames.

The data processing device 120 may obtain a three-dimensional oral cavity model of the object 210 as a whole by merging or aligning a plurality of three-dimensional image frames.

Figure 3:
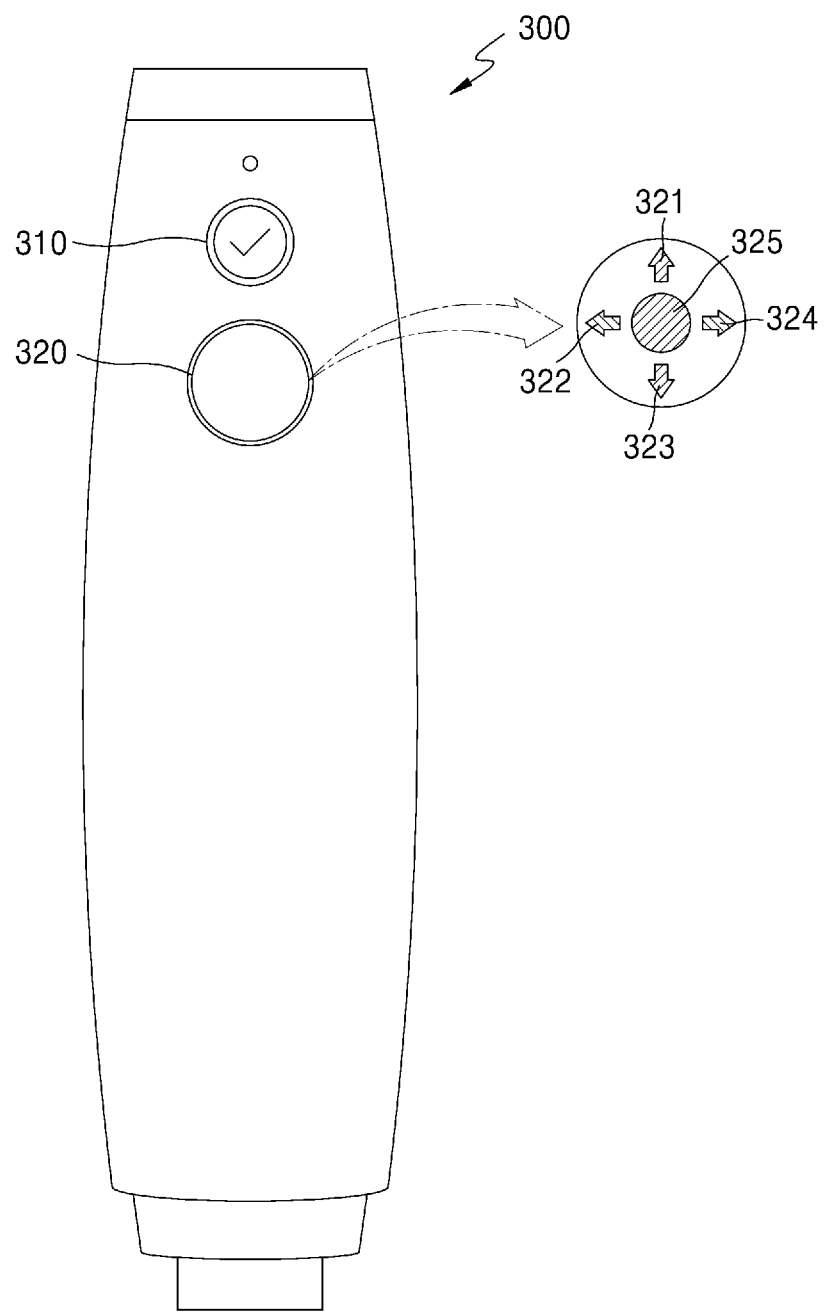
FIG. 3 is a diagram for explaining a user input unit included in a scanner according to an embodiment.

FIG. 3 is a diagram for explaining a user input unit included in a scanner according to an embodiment.

FIG. 3 shows a scanner body. A tip may be detachably fastened to one end of the scanner body. When the scanner is a wired scanner, a cable for connection to a data processing device may be provided at the other end of the scanner body, but is not limited thereto, and the scanner may be implemented as a wireless scanner.

Hereinafter, the scanner body shown in FIG. 3 will be referred to as a scanner 300.

Referring to FIG. 3, a frame or case surrounding the scanner 300 may include a user input unit. The user input unit may receive a user input for controlling the scanner 300 and/or a data processing device connected to the scanner 300. The user input unit may also be referred to as a user interface. A user may control various functions of the scanner 300 and/or the data processing device by using the user input unit provided in the scanner 300.

In an embodiment, the user input unit provided in the scanner 300 may include a scan button 310 and a control button 320.

As a user selects the scan button 310 and/or the control button 320 included in the user input unit, the scanner 300 may obtain a command corresponding to a user input based on the type of button selected by the user and the number of times the button is selected. The scanner 300 may transmit a control signal including a command to the data processing device.

In an embodiment, the control signal transmitted from the scanner 300 to the data processing device may include at least one of information about an operating state of the scanner 300 and control information for controlling the data processing device. The information about the operating state may include at least one of information about whether the scanner 300 is powered on or off, information about whether the scanner 300 operates in a scan mode or a standby mode, and information for identifying the scan mode. Control information for controlling the data processing device may include a remote control signal. The remote control signal may include a signal for changing the display of three-dimensional scan data. The remote control signal may include a signal instructing to output a remote control mode screen.

The data processing device may receive a control signal from the scanner 300 and thus identify an operating state of the scanner 300. Also, the data processing device may operate in response to a control signal from the scanner 300.

In an embodiment, the scan button 310 and/or the control button 320 may be implemented in the form of a physical key or button that receives a user's push operation, or a touch button displayed on a touchpad that detects a touch. However, this is just an example, and the scan button 310 and/or the control button 320 may be implemented in various forms, such as a microphone capable of receiving a user's voice, a sensor capable of recognizing a user's motion as an input, a wheel receiving a user's rotational manipulation, a keyboard, and a dome switch, in addition to a key or a button.

In an embodiment, the scanner 300 may operate in a scan mode or a standby mode depending on whether components included in the scanner 300 are operated while the power is turned on.

In an embodiment, the scanner 300 may operate in a scan mode. The scan mode may refer to a mode in which all components of the scanner 300 are activated and normally operate. A user such as a dentist may obtain raw data or a three-dimensional intraoral image by scanning a patient's oral cavity while the scanner 300 operates in a scan mode.

In an embodiment, the scanner 300 may operate in a standby mode. The standby mode may refer to a state in which power of the scanner 300 itself is turned on, but some components included in the scanner 300, for example, an optical unit, are deactivated. In the standby mode, the optical unit may be in a standby state, and components other than the optical unit may be in an active state. In the standby mode, a communication module (not shown) may perform a network function and thus may transmit/receive a control signal to/from an external device, for example, a data processing device, or transmit information about the operating state of the scanner 300 to the data processing device. The standby mode may also be referred to as an idle mode.

In an embodiment, the scan button 310 may include one key. The scan button 310 may receive a user input for controlling a scan operation of the scanner 300.

In an embodiment, the scan operation controllable using the scan button 310 may include at least one of starting a scan, ending a scan, changing a scan mode, and performing a function previously set by a user in relation to a scan operation.

In an embodiment, the scanner 300 may start a scan operation when receiving a user input to the scan button 310 while operating in a standby mode. For example, when a user clicks the scan button 310 once while the scanner 300 is in a standby mode, the scanner 300 may recognize the user input to the scan button 310 as a command to perform a scan operation, and start the scan operation. The scanner 300 may allow a light source included in a projector to emit light and a camera included in an optical module to obtain a two-dimensional image of an object. The scanner 300 may transmit the obtained two-dimensional image to the data processing device.

In an embodiment, the scanner 300 may stop a scan operation being performed when receiving a user input to the scan button 310 while operating in the scan mode. For example, when a user clicks the scan button 310 once while the scanner 300 is performing a scan, the scanner 300 may recognize the user input to the scan button 310 as a command to stop the scan operation, and stop the scan operation.

In an embodiment, the scan button 310 may receive a user input for changing the scan mode of the scanner 300. The scan mode may be information for identifying an object to be scanned by the scanner 300. The scan mode may be one of an upper jaw scan mode, a lower jaw scan mode, and an occlusion scan mode according to an object to be scanned.

The data processing device does not know whether data received from the scanner 300 is data obtained by scanning the upper jaw, data obtained by scanning the lower jaw, or data obtained by scanning an occlusion in which the upper and lower jaws are bitten. Therefore, a user has to first set a scan mode by using the data processing device and then proceed with the scan. In addition, after the scan of an object is completed, a user has to operate the data processing device and input that the scan of the object is completed. When receiving a user input indicating that scanning is complete, the data processing device performs post-processing on three-dimensional scan data.

However, it is cumbersome and not hygienic to change the scan mode by manipulating the data processing device every time a user wants to change the scan mode or to input that the scan has been completed by manipulating the data processing device.

In an embodiment, a user may change the scan mode by using the scan button 310. For example, a user may change the scan mode by long pressing the scan button 310. The scanner 300 may change the scan mode according to a predetermined order in response to a long press of the scan button 310. For example, the scanner 300 may change the scan mode in the order of upper scan mode, lower scan mode, and occlusion scan mode, but is not limited thereto. When a user wants to scan the lower jaw next after scanning the upper jaw of a patient's oral cavity, the user may long press the scan button 310 to change the scan mode from the upper jaw scan mode to the lower jaw scan mode.

In an embodiment, the scanner 300 may transmit, to the data processing device, information to complete scan data according to the current scan mode, e.g., the upper jaw scan mode, and a control signal notifying that the scan mode is changed to a next scan mode, e.g., the lower jaw scan mode, in response to the user's long-pressing of the scan button 310.

In an embodiment, the data processing device may perform post-processing on the upper jaw scan data according to a control signal received from the scanner 300, and may generate lower jaw scan data based on raw data obtained from the scanner 300 after receiving the control signal.

Therefore, according to an embodiment, when a user wants to end scanning in a scan mode while performing a scan in the scan mode, the user may complete the scan operation according to the current scan mode by long pressing the scan button 310 without separately inputting information indicating that the scan has been completed by manipulating the data processing device. In addition, the user may easily change the scan mode by using the scanner 300.

Operations, in which the scanner 300 photographs an object to obtain two-dimensional image data and the data processing device obtains three-dimensional scan data from the two-dimensional image data and outputs the three-dimensional scan data to the screen, may be performed by executing various options or various functions that may be set. The various options or functions may include, for example, scan depth, scan resolution, whether to perform scan data filtering, whether to perform metal scan, and the like. The various functions may be performed according to values set by default. For example, when the scan depth when the scanner 300 performs a scan is set to 12 mm by default, the scan resolution is set to SD (640×480), and the metal scan is set to off, the scanner 300 may perform scanning at 12 mm and the data processing device may collect and output scan data with a resolution of SD. Also, no metal scan is performed.

In some cases, the user may want the scanner 300 and/or the data processing device to operate according to a value desired by the user, rather than a value set by default, in processing scan data. For example, a user may want a scan depth of 15 mm and a scan resolution of HD (1280×720). Also, the user may want a metal scan to be performed.

In an embodiment, a user may preset setting values for option or function execution to desired values in relation to a scan operation and/or a data processing operation. For example, the user may set the scan depth to be 15 mm, the scan resolution to be HD (1280×720), and the metal scan to be performed, by using the data processing device in advance.

In an embodiment, setting values to execute the option or function set by the user may be matched with the scan button 310 provided in the scanner 300 and stored. When the user clicks the scan button 310 a certain number of times, for example, twice, the scanner 300 and/or the data processing device may perform a scan operation and/or a data processing operation depending on setting values for executing the option and/or function preset by the user. In the above example, when the user presses the scan button 310 twice, the scanner 300 may perform scanning at a depth of 15 mm set by the user, instead of 12 mm set by default, and the data processing device may collect scan data at a resolution of HD rather than SD. Also, the data processing device may perform a metal scan to automatically process a metal surface.

In an embodiment, the data processing device may operate in one of a basic mode and a remote control mode.

In an embodiment, the data processing device may operate in a remote control mode. The remote control mode may mean that the data processing device operates in a remotely controllable form according to a control command through the scanner 300. In the remote control mode, the data processing device may change the display of three-dimensional scan data according to a control signal from the scanner 300. In the remote control mode, the data processing device may output a remote control mode screen.

In an embodiment, the basic mode may mean an operation mode when the data processing device does not operate in the remote control mode. The data processing device may operate in the basic mode as a default when a user input requesting to operate in the remote control mode is not received. Alternatively, when receiving a user input requesting operation in the basic mode while operating in the remote control mode, the data processing device may be switched to the basic mode.

In an embodiment, the control button 320 may receive a user input for controlling the data processing device. A user may use the control button 320 to operate the data processing device in a remote control mode. In addition, the user may control a remote control mode screen, which is output by the data processing device, by using the control button 320.

In an embodiment, while the scanner 300 operates in the scan mode, the control button 320 may be deactivated. In an embodiment, the scanner 300 may receive a user input for the control button 320 only while operating in the standby mode. Therefore, while the scanner 300 is scanning, even when the user inputs the control button 320, an operation according to the input of the control button 320 is not performed.

In an embodiment, the control button 320 may include a plurality of keys. As shown in FIG. 3, the control button 320 may include a four-directional key, that is, four direction keys 321, 322, 323, and 324, and a middle key 325.

In an embodiment, the scanner 300 may receive a user input for the control button 320 while the scanner 300 operates in a standby mode. The scanner 300 may transmit a control signal corresponding to a user input to the data processing device.

In an embodiment, the control signal transmitted from the scanner 300 to the data processing device may include a remote control signal. The remote control signal may be a signal for remotely controlling the data processing device. The remote control signal may include a signal for controlling three-dimensional scan data output from the data processing device. More specifically, the remote control signal may include a signal for controlling a virtual camera that obtains an image of three-dimensional scan data. Also, the remote control signal may include a signal instructing to output a remote control mode screen.

The data processing device may output a remote control screen in response to receiving the remote control signal from the scanner 300.

Alternatively, the user may set the data processing device to output the remote control screen by manipulating the data processing device.

In an embodiment, when the data processing device outputs a remote scan data view screen, the user may select a control type for three-dimensional scan data included in the remote scan data view screen by using the control button 320. In an embodiment, the remote scan data viewing screen may be one of the remote control mode screens output by the data processing device, and may refer to a screen including three-dimensional scan data, which is output in response to the scanner 300 operating in the standby mode. In an embodiment, the remote scan data view screen may include information about control types that may be controlled by the user using the scanner 300. For example, a user may select a control type for three-dimensional scan data by selecting the middle key 325 among the plurality of keys included in the control button 320. The control type for the three-dimensional scan data may include at least one of the movement, rotation, and size change (e.g., enlargement or reduction) of the three-dimensional scan data.

Whenever the user selects/inputs the middle key 325 of the control button 320 provided in the scanner 300, the type of control for three-dimensional scan data included in the remote scan data view screen may be changed.

The user may select/input the four direction keys 321, 322, 323, and 324 in response to the output of the remote scan data view screen including information about a desired control type, thereby allowing the three-dimensional scan data included in the remote scan data view screen to be controlled according to the control type.

In an embodiment, the user may select/input the middle key 325 of the control button 320 a certain number of times in order to view a screen before the three-dimensional scan data is controlled. The data processing device may re-output the remote scan data view screen, which was output before the control of the three-dimensional scan data was performed, according to a user's input.

In an embodiment, the user may long press the middle key 325 of the control button 320. The data processing device may output a screen including an option setting information screen in response to a user input. The option setting information screen may include setting items for at least one of scan settings, scanner settings, data settings, and control settings. A user may select and/or change an item to be set using the four direction keys 321, 322, 323, and 324 and the middle key 325 included in the control button 320.

Figure 4A:
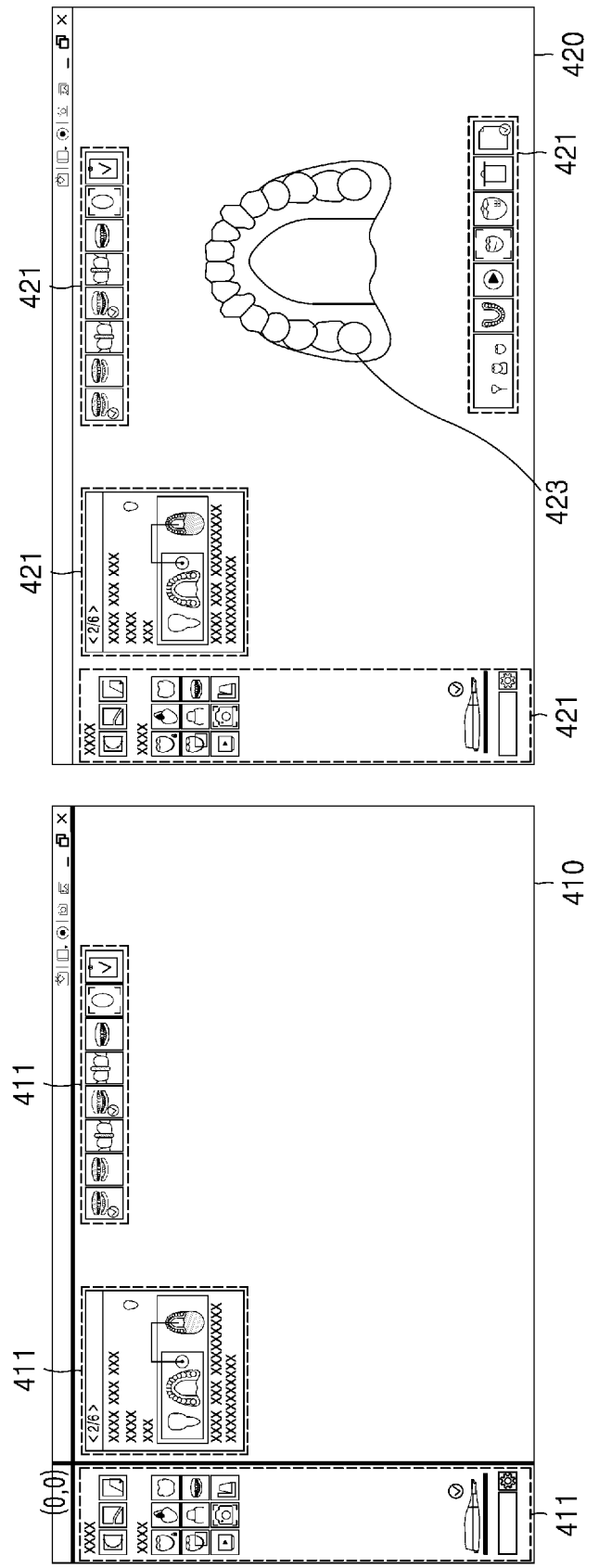
FIGS. 4A and 4B are diagrams for explaining and comparing a screen output when a data processing device operates in a basic mode and a screen output when the data processing device operates in a remote control mode, according to an embodiment.
Figure 4B:
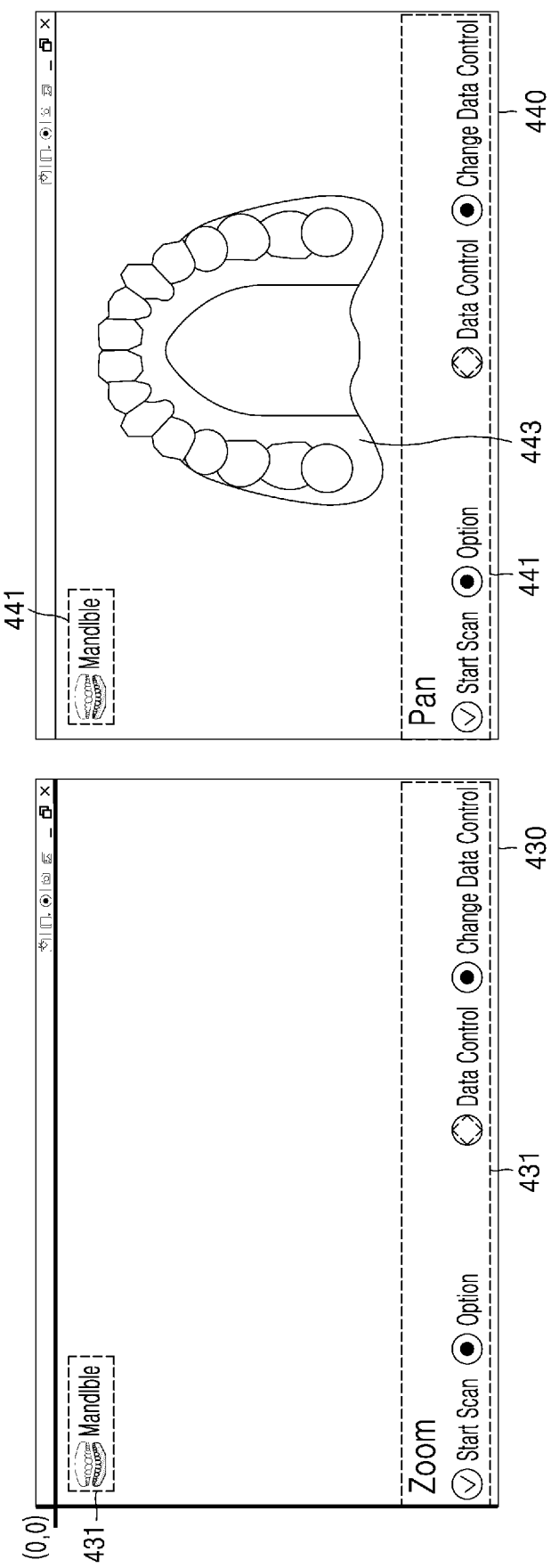

FIGS. 4A and 4B are diagrams for explaining and comparing a screen output when a data processing device operates in a basic mode and a screen output when the data processing device operates in a remote control mode, according to an embodiment.

Referring to FIGS. 4A and 4B, the data processing device may operate in a basic mode or a remote control mode, according to an operation mode.

In an embodiment, a screen output when the data processing device is in the basic mode and a screen output when the data processing device is in the remote control mode may be different from each other. Hereinafter, a screen output when the data processing device is in a basic mode will be referred to as a basic mode screen, and a screen output when the data processing device is in a remote control mode will be referred to as a remote control mode screen.

In an embodiment, the remote control mode screen may include at least one of a remote scanning screen, a remote scan data view screen, a screen for accessing control settings, an option setting information screen, and a remote scan operation selection screen.

FIG. 4A is a diagram illustrating a basic mode screen output when the data processing device operates in the basic mode. A basic mode screen 410 shown on the left side of FIG. 4A is a screen when the data processing device executes scan-related software interworking with a scanner. A basic mode screen 420 shown on the right side of FIG. 4A is a screen on which three-dimensional scan data 423 obtained from two-dimensional image data received from a scanner is output.

As shown in FIG. 4A, the basic mode screens 410 and 420 may respectively include menu bars 411 and 421 including various menus. The menu bars 411 and 421 may include at least one of operation-related information and a user interface (UI). The operation-related information may include information for guiding a shortcut or a key related to data manipulation, which may be input through a keyboard provided in the data processing device. For example, the operation-related information may be information indicating a shortcut key to be manipulated to enlarge, rotate, or move the three-dimensional scan data 423 included in the screen. The user interface may include commands or techniques for operating the data processing device, and may be implemented in the form of icons, text, or images. The user interface may include various tool sets for editing or changing scan data by using the data processing device. For example, the user interface may include menus including enlargement or reduction of scan data, full screen view, previous image view, angle or position change, and the like. Alternatively, the user interface may display whether the scan mode is an upper jaw scan mode, a lower jaw scan mode, or an occlusion scan mode, or may include a menu for selecting the scan mode. Alternatively, the user interface may include a menu for completing the scan mode.

FIG. 4B is a diagram illustrating a remote control mode screen output when the data processing device operates in the remote control mode. A remote control mode screen 430 shown on the left side of FIG. 4B is a screen output by the data processing device when scan-related software is executed, and a remote control mode screen 440 shown on the right side of FIG. 4B is a screen on which three-dimensional scan data 443 obtained from the two-dimensional image data received from a scanner is output.

Comparing FIG. 4A with FIG. 4B, the basic mode screen and the remote control mode screen may differ from each other in at least one of a coordinate system, an output data type, and an output data size.

The coordinate system is a system for determining coordinates that indicate the location of a point in space, and refers to a collective term for a set of origins, reference lengths, reference axes, or reference lines. Because the basic mode screen includes various menu bars 411 and 421, a space in which the three-dimensional scan data 423 may be output is limited. When an area including the three-dimensional scan data 423 is referred to as a scan information area, the basic mode screen has a smaller scan information area than the remote control mode screen.

When a reference point where the scan information area starts on the basic mode screen and the remote control mode screen is expressed as an origin with coordinate values of (0, 0), the location of the origin of the remote control mode screen is located further to the left than the location of the origin of the basic mode screen. Accordingly, the remote control mode screen may include a wider scan information area than the basic mode screen.

When the data processing device outputs the three-dimensional scan data 423 through the basic mode screen, the location and size of the scan information area where the three-dimensional scan data 423 may be output are restricted due to various menu bars 411 and 421, as shown on the right side of FIG. 4A, and thus, the three-dimensional scan data 423 is output in a size smaller than a certain size. Therefore, it is difficult for a user operating the scanner away from the data processing device to easily identify the three-dimensional scan data 423 output on the screen of the data processing device from a distance.

Unlike this, the remote control mode screen does not include the menu bars 411 and 421 included in the basic mode screen, and thus, the remote control mode screen may include, in the scan information area, three-dimensional scan data 443 having a larger size than the basic mode screen. In addition, because the remote control mode screen includes only information indicating the current scan mode or information necessary for the current screen, such as control types 431 and 441 for scan data output on the screen, in a large size, the user may easily identify the current scan mode or control type for scan data even from a distance.

Alternatively, in an embodiment, the remote control mode screen may include a screen including a scan information area as a pop-up screen. When the data processing device outputs the three-dimensional scan data 443 while operating in the remote control mode, the data processing device may output the scan information area, which is an area including the three-dimensional scan data 443, as a pop-up screen separate from an original screen. For example, when the data processing device outputs the three-dimensional scan data 443 while outputting the basic mode screen as shown in FIG. 4A while operating in the remote control mode, the data processing device may output only the scan information area including the three-dimensional scan data 443 as a separate pop-up screen on the basic mode screen. Alternatively, the data processing device may output only the option setting information screen as a separate pop-up screen on the basic mode screen while outputting the basic mode screen as shown in FIG. 4A while operating in the remote control mode.

Also, although not shown in FIGS. 4A and 4B, the remote control mode screen may further include a live view image in addition to the three-dimensional scan data 443 in the scan information area. For example, when a user performs a scan by using a scanner while the data processing device is operating in the remote control mode, the data processing device may output a live view image as well as the three-dimensional scan data 443 onto the remote control mode screen. Because the data processing device outputs the three-dimensional scan data 443 and/or the live view image in a large size while operating in the remote control mode, a user who operates the scanner at a distance from the data processing device may easily identify the three-dimensional scan data 443 and the live view image output on the screen of the data processing device even from a distance.

However, this is just an example, and the data processing device may output the same screen regardless of mode. The data processing device may output the same screen without distinction between when the data processing device does not receive a control signal from the scanner 300 and when the data processing device receives a control signal from the scanner 300 and is controlled accordingly. That is, when the data processing device receives a user input for manipulating a keyboard or mouse provided in the data processing device and operates accordingly, and when the data processing device performs an operation according to a remote control signal from the scanner 300, the data processing device may output a screen having the same coordinate system, type of output data, and size of output data. For example, even when the data processing device receives a user input through an operation key provided in the data processing device and operates accordingly, the data processing device may output a screen having the coordinate system, type of output data, and size of output data in the remote control mode screen described above.

Figure 5:
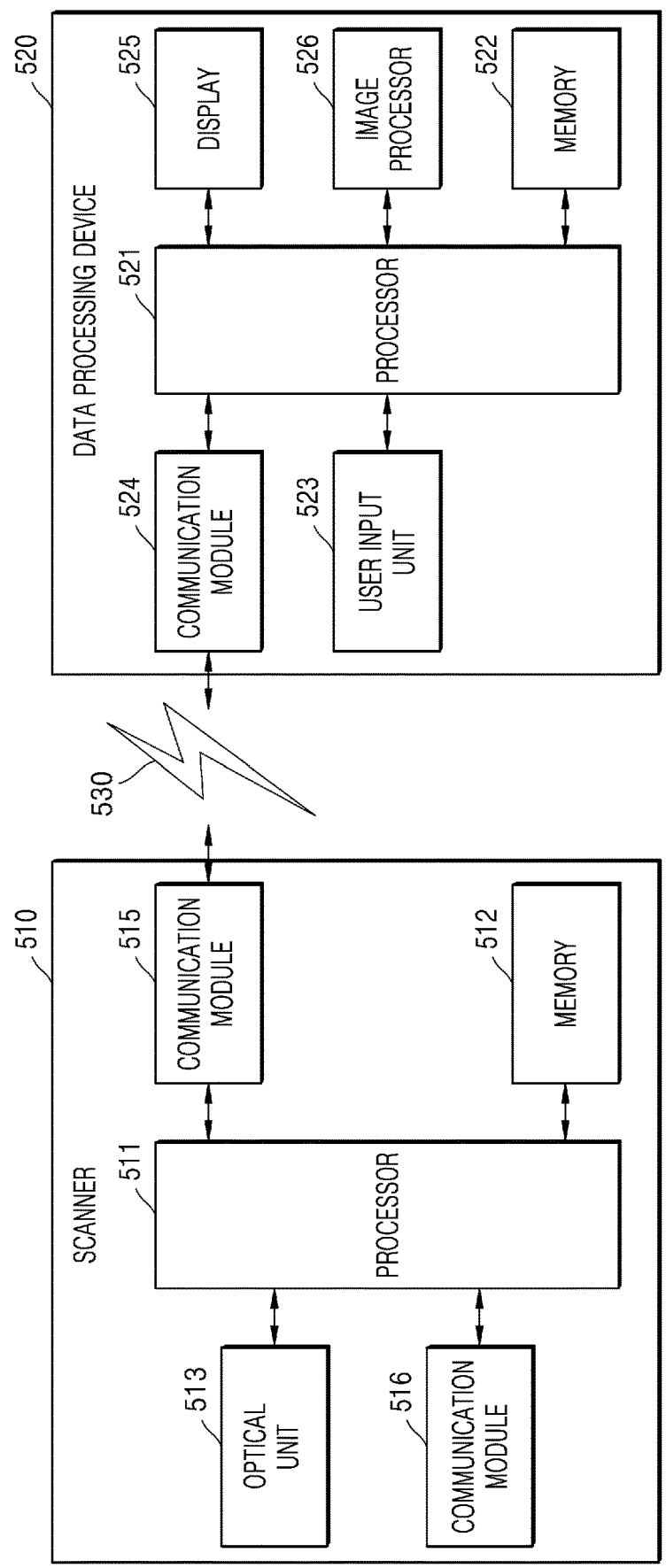
FIG. 5 is an example of a detailed block diagram of a data processing system including a scanner and a data processing device.

FIG. 5 is an example of a detailed block diagram of a data processing system including a scanner and a data processing device.

In an embodiment, the data processing system may include a scanner 510, a data processing device 520, and a communication network 530.

The scanner 510 may obtain raw data by scanning an object. The object may include, for example, a patient's oral cavity or a dental cast model, but is not limited thereto. The scanner 510 may transmit the obtained raw data to the data processing device 520 through the communication network 530, or may process the raw data to generate a three-dimensional virtual model and transmit the three-dimensional virtual model to the data processing device 520.

The scanner 510 may include a processor 511, a memory 512, an optical unit 513, a communication module 515, and a user input unit 516.

The memory 512 may store at least one instruction. Also, the memory 512 may store at least one instruction to be executed by the processor 511. Also, the memory 512 may store at least one program to be executed by the processor 511.

The optical unit 513 may include an optical module and a projector. The optical unit 513 may include a light source, a projector that projects light from the light source, and at least one camera that receives light reflected from an object. The optical unit 513 may project patterned light or structured light. The optical unit 513 may irradiate light with a light source and form a pattern by controlling each of fine mirrors included in a Digital Mirror Device (DMD). The optical unit 513 may irradiate light by controlling the mirrors included in the DMD to be turned on or off. The optical unit 513 may obtain three-dimensional data representing the shape of the object by irradiating light to the object and scanning the object to which the light is irradiated.

The communication module 515 may communicate with the data processing device 520 through a wired or wireless communication network.

In an embodiment, the communication module 515 may transmit a control signal to the data processing device 520. Also, the communication module 515 may transmit information about an operating state of the scanner 510 to the data processing device 520. Also, the communication module 515 may transmit raw data obtained by the optical unit 513 to the data processing device 520.

The communication module 515 may include at least one short-range communication module that performs communication according to communication standards, such as Bluetooth, Wi-Fi, Bluetooth low energy (BLE), NFC/RFID, Wi-Fi Direct, UWB, or ZigBee, a long-range communication module that communicates with a server for supporting long-range communication according to long-range communication standards, and at least one port to be connected to an external electronic device by a wired cable, to communicate with the external electronic device by wire.

The user input unit 516 may receive a user input for controlling the scanner 510. The user input unit 516 may also be referred to as a user interface.

The user input unit 516 may include a touch panel that detects a user's touch, a button that receives a user's push manipulation, a voice recognition device including a microphone, and the like. Alternatively, the user input unit 516 may further include at least one of a wheel or a dome switch that receives a user's rotational manipulation, and a sensor (not shown) capable of recognizing motion.

In an embodiment, the user input unit 516 may include a scan button for receiving a user input for a scan operation and a control button for receiving a user input for remotely controlling the data processing device 520.

In an embodiment, the user may change the operating mode of the scanner 510 from a standby mode to a scan mode or from the scan mode to the standby mode by selecting a scan button included in the user input unit 516. Also, the user may select a scan mode type of the scanner 510 by using a scan button. The scanner 510 may transmit a control signal including identification information about an operating mode of the scanner 510 and a current scan mode to the data processing device 520 according to a user input to a scan button.

In an embodiment, the user may control a remote control mode screen, which is output to the data processing device 520, by selecting a control button included in the user input unit 516.

In an embodiment, the user may control the data processing device 520 operating in a basic mode to operate in the remote control mode by using a control button.

In an embodiment, when a remote scan data view screen is output to the data processing device 520, the user may select a control type for the three-dimensional scan data by using a middle key included in the control button. Control of the three-dimensional scan data may include control of at least one of the movement, rotation, and size change (e.g., enlargement or reduction) of the three-dimensional scan data.

In an embodiment, the user may control the three-dimensional scan data included in the remote scan data view screen by using four direction keys included in the control button.

In an embodiment, the user may select/input the middle key of the control button a certain number of times in order to view a screen before the three-dimensional scan data is controlled. The data processing device 520 may re-output the remote scan data view screen, which was output before the control of the three-dimensional scan data was performed, according to a user's input.

In an embodiment, the user may cause the data processing device 520 to output a screen including an option setting information screen by long pressing the middle key of the control button. The option setting information screen may include a setting menu for at least one of scan settings, scanner settings, data settings, and control settings.

The processor 511 may control the scanner 510 as a whole. The processor 511 may control at least one component included in the scanner 510 to perform an intended operation. Therefore, when the processor 511 performs certain operations, the processor 511 controls at least one of components included in the scanner 700 to perform certain operations. The processor 511 may control the optical unit 513 to obtain three-dimensional data for an object.

In an embodiment, the processor 511 may obtain a control signal according to a user input through the user input unit 516 or receive a control signal from the data processing device 520 and may control the scanner 510 according to the control signal.

In an embodiment, the processor 511 may transmit information about the operating state of the scanner 510 to the data processing device 520 through the communication network 530 in real time.

In an embodiment, the processor 511 may control the data processing device 520 by generating a control signal corresponding to a user input through the user input unit 516 and transmitting the control signal to the data processing device 520.

In an embodiment, the processor 511 may obtain a command corresponding to a user input received through the user input unit 516. The processor 511 may obtain a command corresponding to the user input based on at least one of the type of button selected by the user, the type of key included in the selected button, and the number of times the button or key is selected/input). The processor 511 may notify the data processing device 520 of the operating state of the scanner 510 by generating a control signal including a command and transmitting the control signal to the data processing device 520 through the communication module 515, or may control the data processing device 520 to operate according to a control command.

In an embodiment, the processor 511 may control the scanner 510 to operate the scanner 510 in a scan mode, or in a standby mode, in response to a user's selection of a scan button included in the user input unit 516. Also, the processor 511 may change the scan mode in response to a user input to the scan button. For example, when the current scan mode is an upper jaw scan mode, the processor 511 may complete the upper jaw scan mode in response to a user input to the scan button and control the scanner 510 to operate in a lower jaw scan mode, which is the next scan mode.

In an embodiment, the processor 511 may transmit a control signal corresponding to a control button selection to the data processing device 520 in response to a user's selection of a control button, and thus, the data processing device 520 may operate in the remote control mode.

In an embodiment, when the data processing device 520 outputs a remote scan data view screen, the processor 511 may transmit a control signal corresponding to the control button to the data processing device 520 in response to a user's selection of a middle key included in the control button, and thus, a control type for three-dimensional scan data may be selected.

In an embodiment, the processor 511 may transmit a control signal corresponding to a four-directional key input to the data processing device 520 in response to a user's selection of the four-directional key included in the control button, and thus, three-dimensional scan data included in the remote scan data view screen may be controlled.

In an embodiment, the processor 511 may transmit a control signal corresponding to the control button to the data processing device 520 in response to a user's input of the middle key of the control button a certain number of times, and thus, the data processing device 520 may re-output the remote scan data view screen, which was output before the control of the three-dimensional scan data was performed.

Hereinafter, the data processing device 520 is described. The data processing device 520 may be referred to as an intraoral image processing device.

The data processing device 520 may include a processor 521, a memory 522, a user input unit 523, a communication module 524, a display 525, and an image processor 526.

The user input unit 523 may receive a user input for controlling the data processing device 520. The user input unit 523 may include a user input device including a touch panel for sensing a touch by a user, a button for receiving a push manipulation by a user, a mouse or keyboard for assigning or selecting a point on a user input unit screen, and the like, and may include a voice recognition device for voice recognition, a motion sensor for motion recognition, or the like.

In an embodiment, the user input unit 523 may receive a command from a user to cause the data processing device 520 to operate in the remote control mode.

The communication module 524 may communicate with at least one external electronic device through a wired or wireless communication network. The communication module 524 may communicate with the scanner 510 under the control by the processor 521.

In detail, the communication module 524 may include at least one short-range communication module that performs communication according to communication standards, such as Bluetooth, Wi-Fi, BLE, NFC/RFID, Wi-Fi Direct, UWB, or ZigBee. In addition, the communication module 524 may further include a long-range communication module that communicates with a server for supporting long-range communication according to long-range communication standards.

In addition, the communication module 524 may include at least one port to be connected to an external electronic device, for example, the scanner 510, by a wired cable.

In an embodiment, the communication module 524 may transmit a control signal to the scanner 510. The control signal transmitted to the scanner 510 may include at least one of a power-on or power-off command of the scanner 510 and a command for the scanner 510 to enter a scan mode or a standby mode.

In an embodiment, the communication module 524 may receive information about the current state of the scanner 510 from the scanner 510. The Information about the current state of the scanner 510 may include at least one of information about whether the scanner 510 is in a scan mode or a standby mode and information about which operation of the scan mode the scanner 510 operates in.

In an embodiment, the communication module 524 may receive a control signal from the scanner 510. In an embodiment, the control signal received from the scanner 510 may include a command for the data processing device 520 to operate in a remote control mode.

In an embodiment, the control signal received from the scanner 510 may include a signal for user selection corresponding to the remote control mode screen.

The display 525 may display a certain screen according to the control of the processor 521. The display 525 may output a user interface screen for user input. The display 525 may display a screen including an intraoral image generated based on data obtained by scanning a patient's oral cavity or a plaster model of the oral cavity via the scanner 510. Also, the display 525 may output a three-dimensional oral cavity model generated from two-dimensional image data received from the scanner 510.

In an embodiment, the display 525 may output a basic mode screen in response to the data processing device 520 operating in the basic mode, and output a remote control mode screen in response to the operation of the data processing device 520 in the remote control mode.

In an embodiment, the basic mode screen and the remote control mode screen have different coordinate systems. Because the remote control mode screen does not include various menu bars unlike the basic mode screen, the size of the scan information area of the remote control mode screen is larger than that of the basic mode screen. When a reference point at which the scan information area starts on the remote control mode screen is expressed as the origin having a coordinate value of (0, 0), the location of the origin of the remote control mode screen may be located further left and/or above the location of the origin of the basic mode screen and thus include a wider scan information area on the screen.

In an embodiment, the basic mode screen and the remote control mode screen are different from each other in at least one of output data type and output data size. The remote control mode screen may not include the menu bar included in the basic mode screen, and may also include three-dimensional scan data having a larger size than the basic mode screen. Also, while the scanner 510 operates in the scan mode, the remote control mode screen output by the data processing device 520 may include a live view image received from the scanner 510 in addition to three-dimensional scan data.

The user may identify the operating state of the scanner 510 or the data processing device 520 from a distance by using the remote control mode screen output through the display 525, and accordingly, the user may remotely control the data processing device 520.

The image processor 526 may perform operations for generating and/or processing an image. In detail, the image processor 526 may receive raw data obtained from the scanner 510 and generate a three-dimensional virtual model based on the received data.

The memory 522 may store at least one instruction. In addition, the memory 522 may store at least one instruction to be executed by the processor 521. In addition, the memory 522 may store at least one program to be executed by the processor 521. In addition, the memory 522 may store data (for example, raw data obtained through oral cavity scanning) received from the scanner 510. Alternatively, the memory 522 may store an intraoral image three-dimensionally representing an oral cavity. According to an embodiment, the memory 522 may include one or more instructions for obtaining a three-dimensional oral cavity model from two-dimensional image data.

The processor 521 may control performing of a desired operation by executing at least one instruction stored in the memory 522. The at least one instruction may be stored in an internal memory included in the processor 521 or the memory 522 included in a data processing device, aside from the processor 521.

In an embodiment, the processor 521 may transmit a control signal to the scanner 510 by executing one or more instructions stored in the memory 522, so that the scanner 510 is controlled according to the control signal. The processor 521 may operate according to a control signal input by the user through the scanner 510 in response to the remote control mode screen output through the display 525.

In an embodiment, the processor 521 may control the display 525 according to a control signal from the scanner 510 so that the display 525 outputs a remote control mode screen.

In an embodiment, the processor 521 may output a remote scan data view screen capable of controlling three-dimensional scan data through the display 525 according to a control signal from the scanner 510.

In an embodiment, the processor 521 may receive a control type selection for three-dimensional scan data according to a control signal from the scanner 510.

In an embodiment, the processor 521 may rotate or move three-dimensional scan data included in the remote scan data view screen or change the size of the three-dimensional scan data, according to a control signal from the scanner 510.

In an embodiment, the processor 521 may output, through the display 525, a remote scan data view screen before the three-dimensional scan data is controlled, according to a control signal from the scanner 510.

According to an embodiment, the performing of operations such as "extraction," "obtaining," "generating," and the like, by the processor 521, may include not only directly performing the above-described operations by executing at least one instruction in the processor 521, but also controlling other constituent elements to perform the above-described operations.

In order to implement the embodiments disclosed herein, the scanner 510 and the data processing device 520 may include only some of the components shown in FIG. 5 or may include more components than the components shown in FIG. 5.

In addition, the data processing device 520 may store and execute dedicated software linked to the scanner 510. The dedicated software may also be referred to as a dedicated program, a dedicated tool, or a dedicated application. When the data processing device 520 operates in conjunction with the scanner 510, the dedicated software stored in the data processing device 520 may be connected to the scanner 510 to receive, in real time, data obtained through oral cavity scanning.

In addition, the dedicated software may transmit and receive control signals to and from the scanner 510, and may also perform at least one operation for obtaining, processing, storing, and/or transmitting an intraoral image. The dedicated software may be stored in the processor 521. Also, the dedicated software may provide a remote control mode screen. The remote control mode screen provided by the dedicated software may include a screen for selecting a control signal according to the disclosed embodiment or a screen for outputting a live view image and/or three-dimensional scan data obtained by the scanner 510.

Figure 6A:
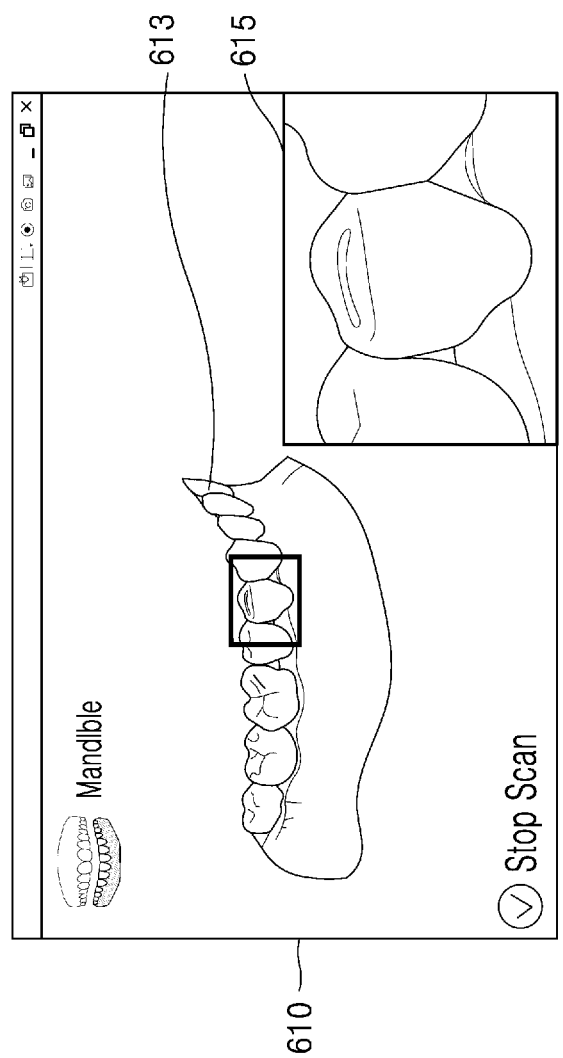
FIGS. 6A and 6B are diagrams illustrating that a data processing device outputs a remote scanning screen, according to an embodiment.
Figure 6B:
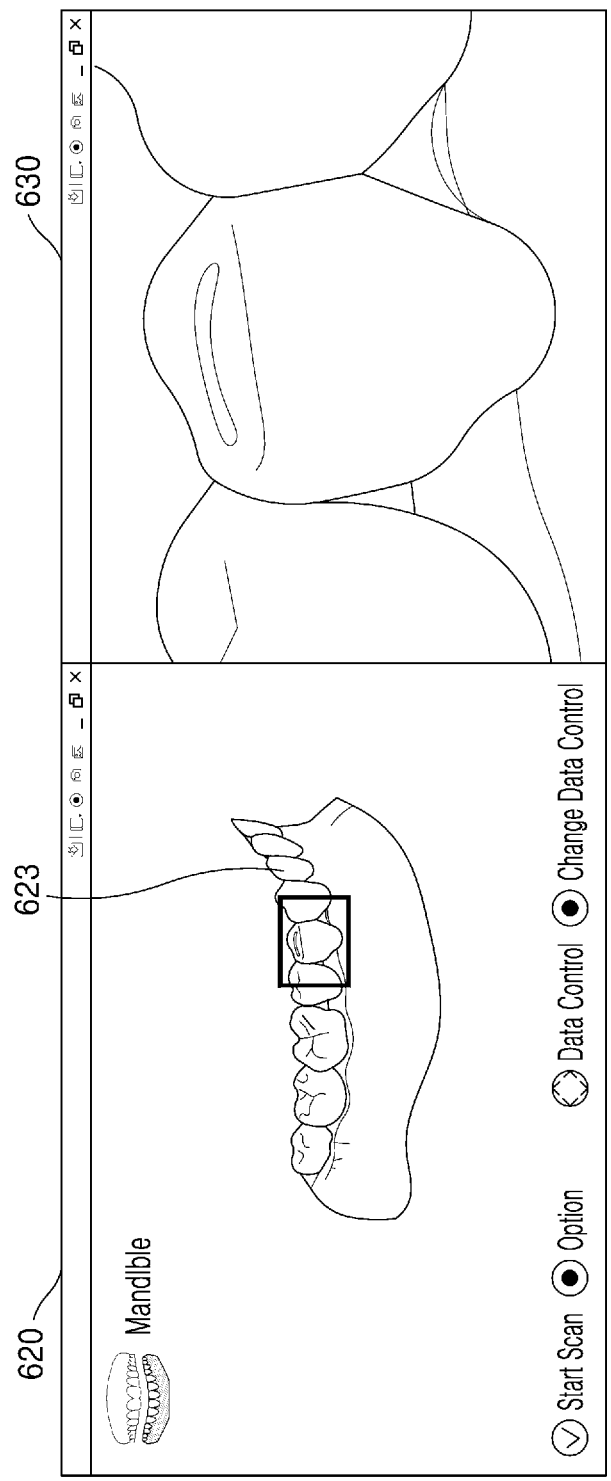

FIGS. 6A and 6B are diagrams illustrating that a data processing device outputs a remote scanning screen, according to an embodiment.

In an embodiment, the data processing device may operate in a remote control mode.

In an embodiment, the data processing device may operate in a remote control mode based on a user input through a control button included in a scanner. Alternatively, in an embodiment, the data processing device may operate in the remote control mode based on selection to operate in the remote control mode through a user input unit included in the data processing device.

In an embodiment, the data processing device may output a remote control mode screen while operating in the remote control mode.

In an embodiment, while the data processing device operates in the remote control mode, a user may issue a command to start a scan operation by using a scan button provided in the scanner. For example, a user may issue a command to start a scan operation by clicking once a scan button provided in the scanner while the scanner is operating in a standby mode.

The scanner may generate a control signal corresponding to a user command to start a scan operation and transmit the control signal to the data processing device.

Also, the scanner may operate in a scan mode according to a user command to start a scan operation. The scanner may project light onto an object and receive light reflected from the object by using a camera to obtain a live view image. The scanner may transmit a live view image of the object obtained using the camera to the data processing device. Also, the scanner may obtain raw data of the object or three-dimensional data representing the shape of the object, and transmit the raw data and the three-dimensional data to the data processing device.

In an embodiment, when receiving a control signal including a scan command from the scanner while operating in the remote control mode, the data processing device may output a remote scanning screen in response to the control signal.

In an embodiment, the remote scanning screen may be one of remote control mode screens output while the data processing device is operating in the remote control mode, and may refer to a screen that outputs, in a large size, data obtained from a scanner operating in a scan mode so that a user may easily recognize the data.

In an embodiment, the data obtained from the scanner may include a two-dimensional image and three-dimensional scan data of the object. That is, in an embodiment, the remote scanning screen may include a two-dimensional image of the object obtained by the scanner in real time, that is, a live view image. Also, in an embodiment, the remote scanning screen may include three-dimensional scan data obtained based on raw data obtained by the scanner.

FIGS. 6A and 6B are views illustrating remote scanning screens.

In an embodiment, as shown in FIG. 6A, the data processing device may output both three-dimensional scan data 613 and a live view image 615 on one remote scanning screen 610. In the three-dimensional scan data 613, an area of the object currently being scanned by the scanner may be displayed in a frame shape or the like. The area of the object currently being scanned by the scanner may be the same area as the area shown in the live view image 615.

In an embodiment, the sizes of the live view image 615 and the three-dimensional scan data 613 included in the remote scanning screen 610 may be adjusted. The user may set the size of the live view image to be included in the remote scanning screen to a desired size by manipulating the data processing device in advance. As the size of the live view image increases, the size of the three-dimensional scan data relatively decreases. Accordingly, the user may set the size of the live view image on the remote scanning screen so that the size of the live view image is within a certain range. For example, the user may adjust the size of the live view image to a desired size within a range of about ¼ to about ½ of the horizontal and vertical lengths of the remote control mode screen.

When the size of the live view image is adjusted, the location and size of the three-dimensional scan data included in the remote scanning screen are also adjusted accordingly. For example, the center of the three-dimensional scan data may be located at the center of the horizontal length remaining except for the horizontal length of the live view image on the remote scanning screen, and the three-dimensional scan data may be adjusted to a size that does not overlap the live view image.

In an embodiment, as shown in FIG. 6B, the remote scanning screen output by the data processing device may be output through two windows 620 and 630. The data processing device may output the three-dimensional scan data 613 and the live view image 615 through separate windows 620 and 630, respectively.

Alternatively, in an embodiment, although not shown in FIGS. 6A and 6B, the remote scanning screen output by the data processing device may be output through two monitors. For example, when the data processing device has dual monitors, the data processing device may output three-dimensional scan data through one monitor and output a live view image through the other monitor.

The user may manipulate the data processing device in advance to set whether to output the remote scanning screen in one window or two windows or whether to output the three-dimensional scan data and the live view image through separate monitors by using dual monitors.

Because the remote scanning screen does not include a menu bar for editing scan data, the three-dimensional scan data and the live view image may be largely included in the remote scanning screen. Therefore, even when the user performs scanning at a location far from the data processing device, the user may view the live view image in a large size through the remote scanning screen output from the data processing device, and thus, it may be easily identified which part of the object is currently scanned by the user. In addition, because the user may view the three-dimensional scan data in a large size through the remote scanning screen, whether the scan operation of the object is being performed well may be easily checked.

Figure 7:
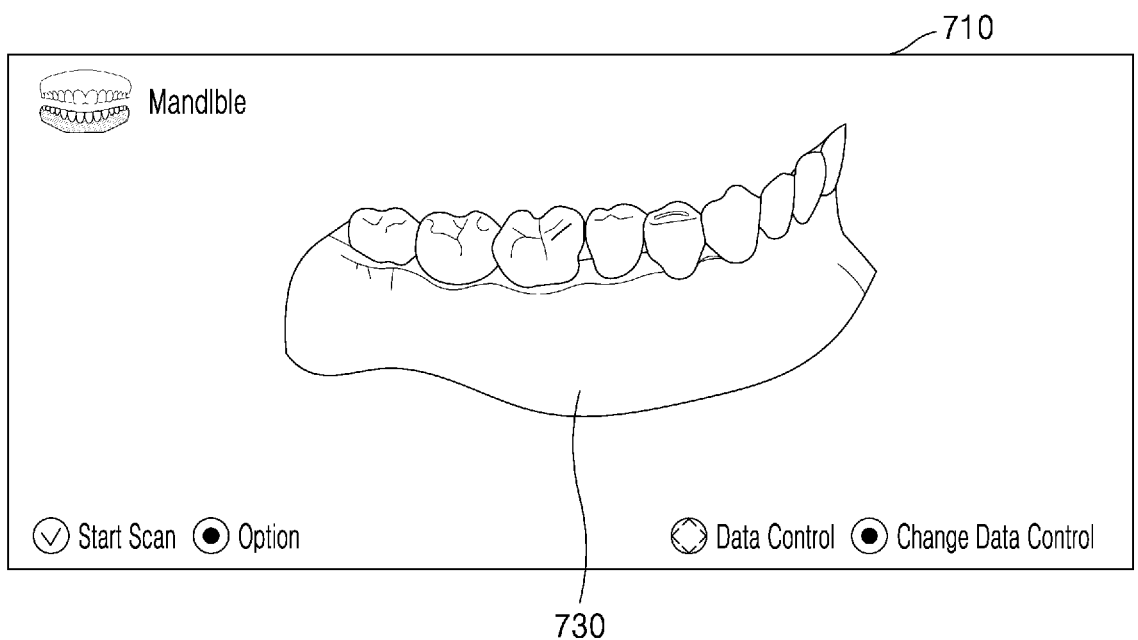
FIG. 7 is a diagram illustrating that a data processing device outputs a remote scan data view screen, according to an embodiment.

FIG. 7 is a diagram illustrating that a data processing device outputs a remote scan data view screen, according to an embodiment.

In an embodiment, the data processing device may receive a scan end command from a user while outputting a remote scanning screen. For example, the data processing device may receive a control signal from a scanner to end scanning. A user may input a user command to end scanning by selecting a scan button provided in the scanner while the scanner operates in a scan mode.

In an embodiment, the data processing device may output a remote scan data view screen in response to receiving a scan end command.

In an embodiment, the remote scan data view screen may be one of remote control mode screens output while the data processing device operates in the remote control mode, and may refer to a screen output in response to the scanner operating in the standby mode.

When the scan operation ends while operating in the remote control mode, the data processing device may output a remote scan data view screen to provide the user with three-dimensional scan data in more detail.

FIG. 7 is a diagram illustrating a remote scan data view screen 710. Referring to FIG. 7, it may be seen that the remote scan data view screen 710 includes three-dimensional scan data 730 in a large size in the center of the screen.

In an embodiment, the remote scan data view screen 710 may include only three-dimensional scan data 730 and not a live view image, unlike the remote scanning screen. Accordingly, the three-dimensional scan data 730 included in the remote scan data view screen 710 may be located in the center of the screen and may be output in a larger size than the three-dimensional scan data included in the remote scanning screen.

The user may check whether the scan has been successfully performed using the remote scan data view screen 710. More specifically, the user may examine the three-dimensional scan data 730 included in the remote scan data view screen 710 in detail by controlling the three-dimensional scan data 730 by using a scanner.

A user's control of three-dimensional scan data by using a scanner will be described below with reference to FIGS. 8A-8C.

Figure 8A:
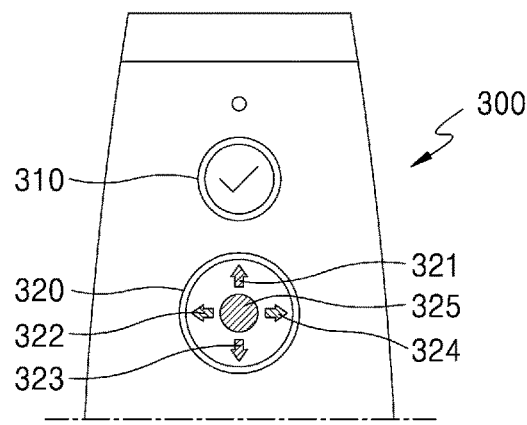
FIGS. 8A to 8C are diagrams for explaining how a user controls three-dimensional scan data included in a remote scan data view screen by using a scanner, according to an embodiment.
Figure 8A:
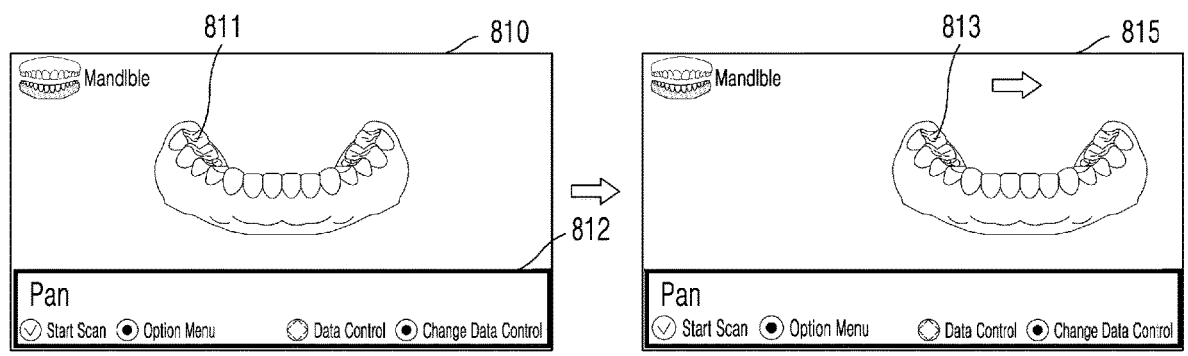
Figure 8B:
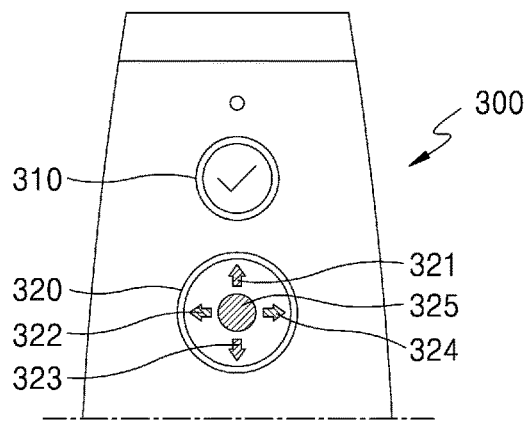
Figure 8B:
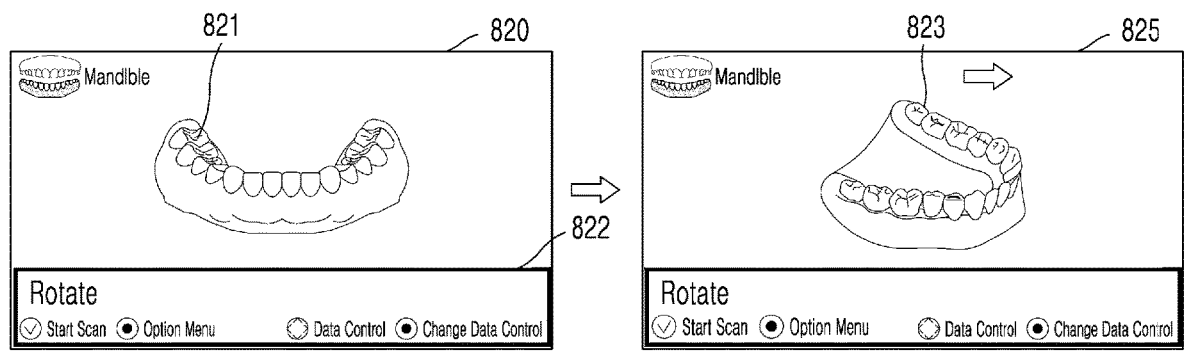
Figure 8C:
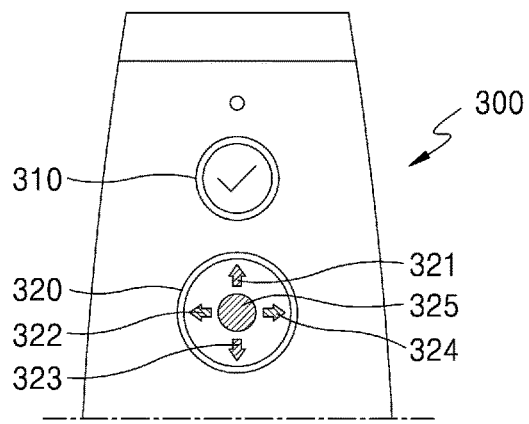
Figure 8C:
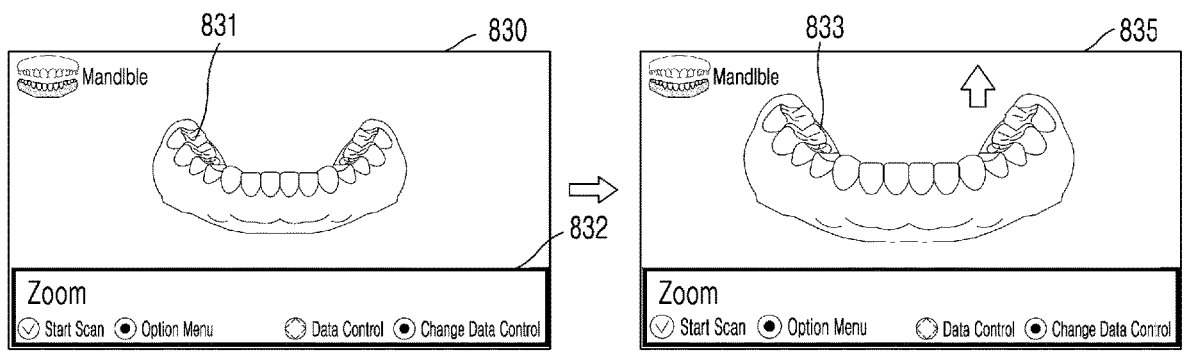

FIGS. 8A to 8C are diagrams for explaining how a user controls three-dimensional scan data included in a remote scan data view screen by using a scanner, according to an embodiment.

As a scanner 300 shown in FIGS. 8A to 8C is the same as the scanner 300 shown in FIG. 3, the same reference numerals are used therefor. Hereinafter, descriptions that are redundant with those given with reference to FIG. 3 are omitted.

A user may terminate a scan operation by selecting a scan button 310 while the scanner 300 is operating in a scan mode.

In an embodiment, the data processing device may output a remote scan data view screen when a scan operation is terminated while operating in a remote control mode. The remote scan data view screen may include three-dimensional scan data in a state in which scanning is finished.

In an embodiment, when the data processing device outputs the remote scan data view screen, the user may select a control type for three-dimensional scan data included in the remote scan data view screen. For example, a user may select a control type for three-dimensional scan data by selecting a middle key 325 among a plurality of keys included in a control button 320.

In an embodiment, the type of control for the three-dimensional scan data included in the remote scan data view screen may include at least one of the movement of the three-dimensional scan data, the rotation of the three-dimensional scan data, and the size change of the three-dimensional scan data.

In an embodiment, the remote scan data view screen may include information about control types that may be controlled by the user by using the scanner 300.

In an embodiment, whenever the user selects/inputs the middle key 325 of the control button 320 provided in the scanner 300 in response to the data processing device outputting the remote scan data view screen, the data processing device may change the control type for the three-dimensional scan data included in the remote scan data view screen. The user may select a desired control type by selecting/inputting the middle key 325 of the control button 320 a certain number of times.

The user may select the four direction keys 321, 322, 323, and 324 in response to the output of the remote scan data view screen including information about a desired control type, thereby allowing the three-dimensional scan data included in the remote scan data view screen to be controlled according to the control type.

FIG. 8A is a diagram illustrating the movement of three-dimensional scan data 811 according to a user input when a control type for the three-dimensional scan data 811 is 'Pan (i.e., movement)' according to an embodiment.

Referring to FIG. 8A, a remote scan data view screen 810 may include control type information 812 indicating that the control type for the three-dimensional scan data 811 is 'Pan (i.e., movement)'. The user may know that the control type is the movement (i.e., Pan) of the three-dimensional scan data 811 by using the control type information 812.

The data processing device may output a screen, in which the three-dimensional scan data 811 moves to the right, left, up, or down from the current location, in response to the user inputting the four direction keys 321, 322, 323, and 324 included in the control button 320 of the scanner 300. For example, when the user selects a right direction key 324 among the four direction keys 321, 322, 323 and 324 while viewing the remote scan data view screen 810 on the left side of FIG. 8A, the data processing device may output a remote scan data view screen 815 including three-dimensional scan data 813 moved to the right more than the original location, as shown on the right side of FIG. 8A.

When the user presses the right direction key 324 several times, the data processing device may output a screen in which the three-dimensional scan data 813 continuously moves to the right. When the user continues to press and hold the right direction key 324, the data processing device may output a screen in which the three-dimensional scan data 813 continues to move to the right until the three-dimensional scan data 813 can no longer move to the right.

In an embodiment, when the user changes the control type for the three-dimensional scan data 811 from 'Pan' to 'Rotate' by selecting the middle key 325 of the control button 320 in the scanner 300 while the data processing device is outputting the remote scan data view screen 810 shown on the left side of FIG. 8A, the data processing device may output a remote scan data view screen 820 shown in FIG. 8B.

FIG. 8B is a diagram illustrating the rotation of three-dimensional scan data 821 according to a user input when a control type for the three-dimensional scan data 821 is 'Rotate', according to an embodiment.

Referring to FIG. 8B, the remote scan data view screen 820 may include control type information 822 indicating that the control type for the three-dimensional scan data 821 is 'Rotate'.

The data processing device may output a screen, in which the three-dimensional scan data 821 rotates to the right, left, up, or down, in response to the user inputting the four direction keys 321, 322, 323, and 324 included in the control button 320 of the scanner 300. For example, when the user selects the right direction key 324 among the four direction keys 321, 322, 323 and 324 while viewing the remote scan data view screen 820 on the left side of FIG. 8B, the data processing device may output a remote scan data view screen 825 including three-dimensional scan data 823 rotated to the right from the original direction, as shown on the right side of FIG. 8B.

In an embodiment, when the user selects the middle key 325 of the control button 320 provided in the scanner 300 while the data processing device outputs the remote scan data view screen 820 shown on the left side of FIG. 8B, the control type for the three-dimensional scan data 821 may be changed from 'Rotate' to 'Zoom' and the data processing device may output a remote scan data view screen 830 shown in FIG. 8C.

FIG. 8C is a diagram for explaining that the three-dimensional scan data 831 is enlarged or reduced according to a user input when the control type for the three-dimensional scan data 831 is 'Zoom', according to an embodiment.

Referring to FIG. 8C, the remote scan data view screen 830 may include control type information 832 indicating that the control type for the three-dimensional scan data 831 is 'Zoom'.

In response to the user selecting an up key 321 or a down key 323 from among the four direction keys 321, 322, 323, and 324 included in the control button 320 of the scanner 300, the data processing device may enlarge or reduce and output the three-dimensional scan data 831. For example, when the user selects the up key 321 of the four direction keys 321, 322, 323, and 324 while the data processing device outputs the remote scan data view screen 830 on the left side of FIG. 8C, the data processing device may output a remote scan data view screen 835 including three-dimensional scan data 833 enlarged than the original size, as shown on the right side of FIG. 8C.

In an embodiment, after three-dimensional scan data included in the remote scan data view screen is controlled according to the user's control, the user may press the middle key 325 included in the control button 320 of the scanner 300 a certain number of times, and thus, the data processing device may re-output the remote scan data view screen before the three-dimensional scan data is controlled.

For example, after the user selects the right direction key 324 among four direction keys 321, 322, 323, and 324 while viewing the remote scan data view screen 810 on the left side of FIG. 8A and the data processing device outputs the remote scan data view screen 815 including the three-dimensional scan data 813 moved to the right more than the original location, as shown on the right side of FIG. 8A, when the user double-clicks the middle key 325 included in the control button 320 of the scanner 300, the data processing device may re-output the remote scan data view screen 810 on the left side of FIG. 8A, in which the three-dimensional scan data 811 is located in the original location before being controlled, that is, in the center of the screen.

In an embodiment, the data processing device may output a screen in which the three-dimensional scan data 811 is controlled, in response to the user pressing the four direction keys 321, 322, 323, and 324 included in the control button 320 of the scanner 300, and then may re-output a remote scanning screen, which had previously been output and then stopped, in response to the user pressing the scan button 310 of the scanner 300. That is, the data processing device may output the remote scanning screen in response to the user performing the scan operation by using the scanner 300, and then may re-output the remote scanning screen that was outputted at the time of stopping the scan operation, in response to a user's scan stop command. The remote scanning screen that is output again may include both three-dimensional scan data and a live view image. The user may continue the previously stopped scan operation while viewing the remote scanning screen output by the data processing device.

Figure 9A:
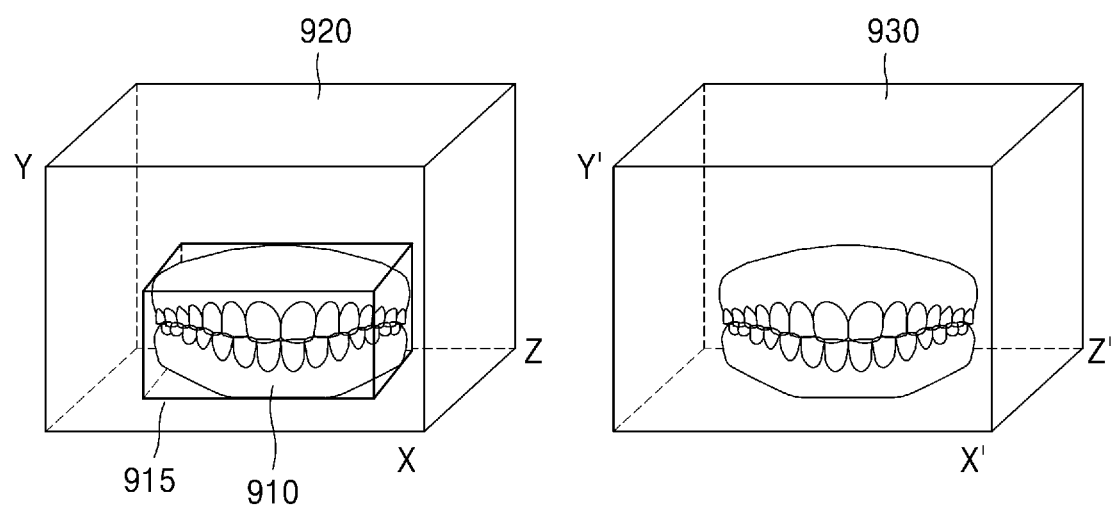
FIGS. 9A to 9C are diagrams for explaining that a data processing device generates a screen on which three-dimensional scan data is controlled, according to an embodiment.
Figure 9B:
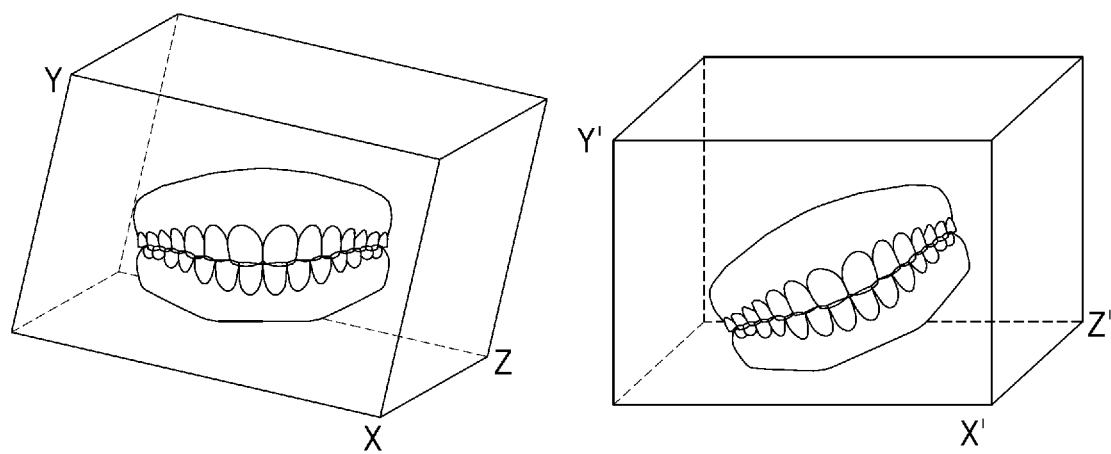
Figure 9C:
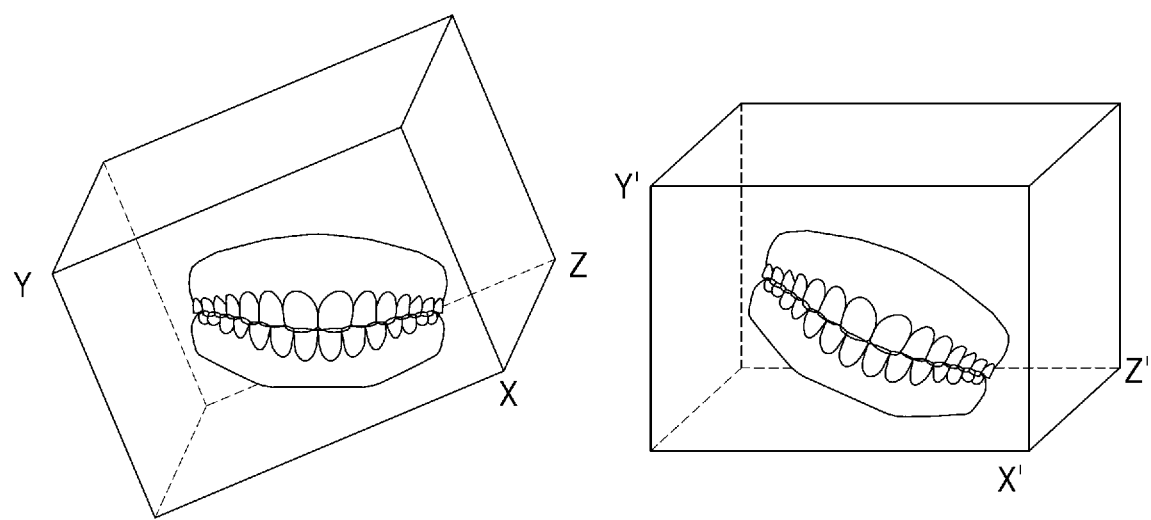

FIGS. 9A to 9C are diagrams for explaining that a data processing device generates a screen on which three-dimensional scan data is controlled, according to an embodiment.

In an embodiment, the data processing device may use a virtual camera to generate a screen on which three-dimensional scan data included in a remote scan data view screen is controlled.

In an embodiment, the virtual camera may operate in response to a control type and a user input for a four-directional key of a control button provided in a scanner.

In an embodiment, the virtual camera may rotate or move according to the control type and the user input to the control button, or enlarge or reduce the three-dimensional scan data, and obtain an image of the three-dimensional scan data by photographing the three-dimensional scan data captured at the location of the virtual camera.

In an embodiment, the data processing device may generate a screen, on which the three-dimensional scan data is controlled, by outputting, through a remote scan data view screen, an image of the three-dimensional scan data obtained by the virtual camera.

For example, it is assumed that the data processing device is outputting a remote scan data view screen and the control type is 'Pan (i.e., movement)'. The user may move the three-dimensional scan data in up, down, left, and right directions by inputting a desired direction key among the four direction keys of the control button provided in the scanner while viewing the remote scan data view screen output to the data processing device. In this case, it appears to the user that the three-dimensional scan data moves according to the four-directional key input of the control button, but in reality the three-dimensional scan data does not move and the virtual camera that photographs the three-dimensional scan data may move.

In an embodiment, the virtual camera may move in a virtual coordinate system according to a user input through the scanner. The virtual camera may obtain an image of the three-dimensional scan data by photographing the right side, left side, top side, bottom side, etc. of the fixed three-dimensional scan data while moving in the virtual coordinate system. For example, when the user selects the right key among the four direction keys, the virtual camera may obtain an image of the three-dimensional scan data by photographing the three-dimensional scan data while moving to the left in the virtual coordinate system. The data processing device may output, through the remote scan data view screen, an image of the three-dimensional scan data obtained while the virtual camera moves to the left. In this case, it appears to the user that the three-dimensional scan data moves to the right in response to an input to the right key of the four direction keys.

For example, it is assumed that the data processing device is outputting a remote scan data view screen, the control type is 'Rotate', and the user rotates the three-dimensional scan data by using the four direction keys of the control button.

In an embodiment, the virtual camera may rotate in a virtual coordinate system in response to a user input using a scanner.

The virtual camera may obtain a rotational image of the three-dimensional scan data by photographing the front, side, back, top, bottom, etc. of the fixed three-dimensional scan data while rotating in a virtual coordinate system. The data processing device may output, through a remote scan data view screen, an image of the three-dimensional scan data obtain by the virtual camera. In this case, it appears to the user that the three-dimensional scan data rotates according to the four-directional key input of the control button, but in reality, the three-dimensional scan data does not rotate and the virtual camera that photographs the three-dimensional scan data rotates in a direction opposite to the four-directional key input.

FIGS. 9A to 9C is diagrams for explaining a comparison between an image of three-dimensional scan data obtained using a virtual camera and an image of three-dimensional scan data output through a screen of a data processing device.

In the drawing shown on the left side of FIG. 9A, a bounding box 915 surrounding three-dimensional scan data 910 is shown. The bounding box 915 is a virtual box generated according to the size of the three-dimensional scan data 910, and may have a size corresponding to a length on the X axis, a length on the Y axis, and a length on the Z axis of the three-dimensional scan data 910. For example, the bounding box 915 may be a hexahedral box having the same length as maximum lengths on the X, Y, and Z axes of the three-dimensional scan data 910, as corners of the X, Y, and Z axes.

The center of the three-dimensional scan data 910 may be the center of the bounding box 915. When the control type is Rotate' and the user inputs a user input for rotating the three-dimensional scan data by using the four direction keys of the control button provided in the scanner, the scanner may generate a remote control signal for rotating the three-dimensional scan data and transmit the remote control signal to the data processing device. The data processing device may control the virtual camera according to the remote control signal. The data processing device may allow the virtual camera to photograph three-dimensional scan data 910 while rotating outside a virtual sphere made by connecting the bounding box 915, based on the center of the bounding box 915.

In an embodiment, when there are a plurality of pieces of three-dimensional scan data spaced apart from each other, the bounding box may be a hexahedral box including all of the plurality of pieces of three-dimensional scan data and having a minimum length enclosing the plurality of pieces of three-dimensional scan data. The virtual camera may photograph a plurality of pieces of three-dimensional scan data while rotating out of the bounding box, based on a central point of one of the plurality of pieces of three-dimensional scan data.

The drawings shown on the left sides of FIGS. 9A, 9B, and 9C are diagrams for explaining that a virtual camera captures three-dimensional scan data in a virtual coordinate system. The three-dimensional scan data 910 may be fixed, and the virtual camera may capture the three-dimensional scan data 910 while operating. In the drawings shown on the left sides of FIGS. 9A, 9B, and 9C, a first box 920 may represent a virtual area captured by a lens of the virtual camera.

The drawing shown on the left side of FIG. 9A shows a composition in which the virtual camera captures the front of the three-dimensional scan data. The drawing shown on the left side of FIG. 9B shows a composition when the virtual camera captures the three-dimensional scan data in a state where the lens of the camera is tilted in the lower right direction of the three-dimensional scan data. The drawing shown on the left side of FIG. 9C shows a composition when the virtual camera captures the three-dimensional scan data in a state where the lens is tilted in the lower left direction of the three-dimensional scan data.

The drawings shown on the right sides of FIGS. 9A, 9B, and 9C are diagrams illustrating three-dimensional scan data output from the data processing device. In the drawings shown on the right sides of FIGS. 9A, 9B, and 9C, a second box 930 surrounding the three-dimensional scan data 910 may indicate an output area output through the display of the data processing device. Because the user sees the output area output by the data processing device, it is recognized that the three-dimensional scan data 910 operates as in the drawings shown on the right sides of FIGS. 9A, 9B, and 9C.

The data processing device may adjust and output the three-dimensional scan data obtained by the virtual camera to fit the screen of the data processing device. The data processing device may adjust the direction, angle, position, or the like of the first box 920, which is an area captured by the lens of the virtual camera, to match the second box 930, which is an output area of the display of the data processing device, and may output the adjusted result. More specifically, as shown on the left sides of FIGS. 9A, 9B, and 9C, the data processing device may match coordinate values on the X, Y, and Z axes of the three-dimensional scan data 910 included in the first virtual box 920 with coordinate values on the X', Y', and Z' axes of the second box 930 output through the display of the data processing device and output three-dimensional scan data through a display.

In this case, the three-dimensional scan data output through the screen of the data processing device appears to operate in the opposite direction to that of the virtual camera. That is, to the user, as shown on the right side of FIG. 9B, the three-dimensional scan data appears to be tilted in the lower left direction, and as shown on the right side of FIG. 9C, the three-dimensional scan data appears to be tilted in the lower right direction.

Figure 10:
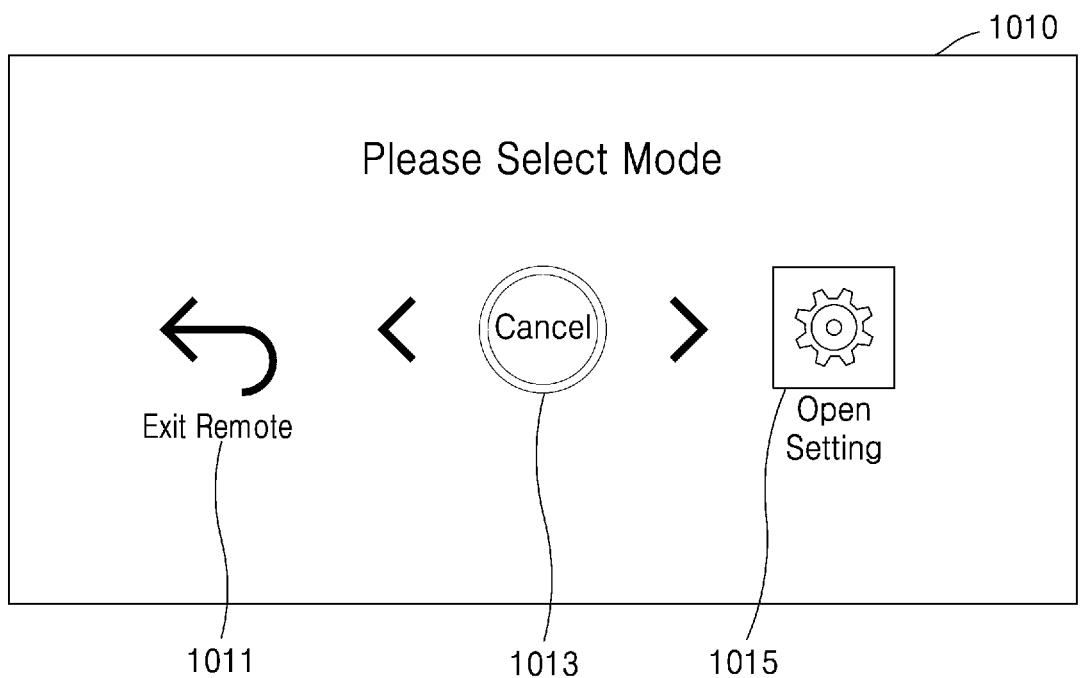
FIG. 10 is a diagram illustrating that a data processing device outputs a screen through which various control settings may be accessed, according to an embodiment.

FIG. 10 is a diagram illustrating that a data processing device outputs a screen through which various control settings may be accessed, according to an embodiment.

In an embodiment, while operating in a remote control mode, the data processing device may output a screen 1010 for accessing control settings, as shown in FIG. 10, in response to a user's long press of a central key of a control button provided in the scanner.

In an embodiment, the screen 1010 through which control settings may be accessed is one of remote control mode screens, and may include various setting information. The setting information may include at least one of setting information 1011 commanding the data processing device to switch to a basic mode, setting information 1013 for canceling the current screen, exiting the current screen, and returning to the previously output screen, and option setting information 1015 for changing setting values related to scanners, scanning, data processing, etc.

The user may move to desired setting information among setting information included in the screen 1010, through which control settings may be accessed, by using four direction keys of a control button provided in the scanner, in response to the data processing unit outputting the screen 1010 through which control settings may be accessed. The user may select desired setting information by inputting/pressing the middle key of the control button provided in the scanner. The data processing device may operate in response to the setting information selected by the user or output a screen according to the setting information selected by the user.

Figure 11A:
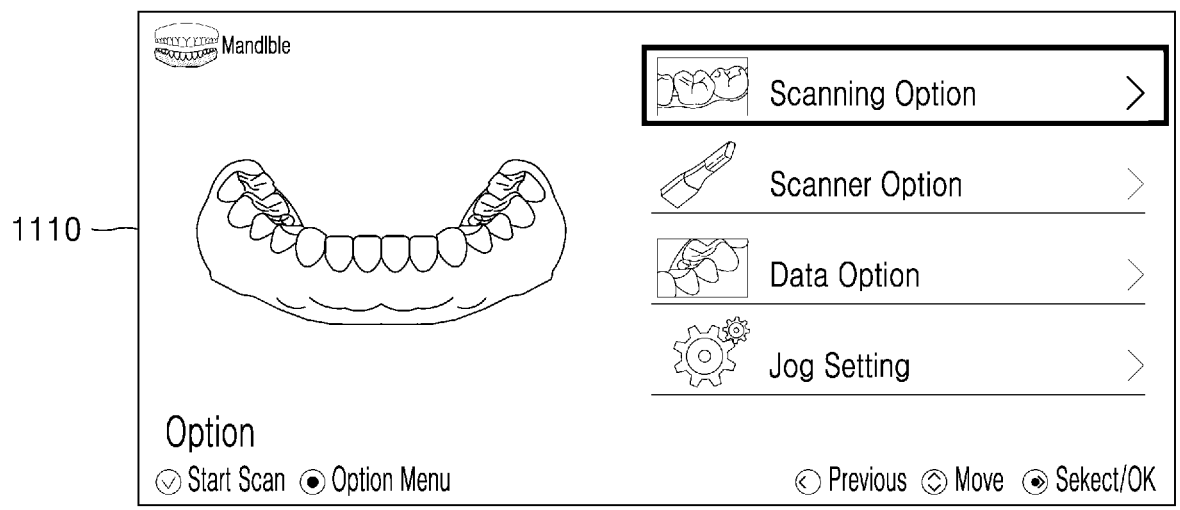
FIGS. 11A to 11C are diagrams illustrating an option setting information screen output by a data processing device, according to an embodiment.
Figure 11B:
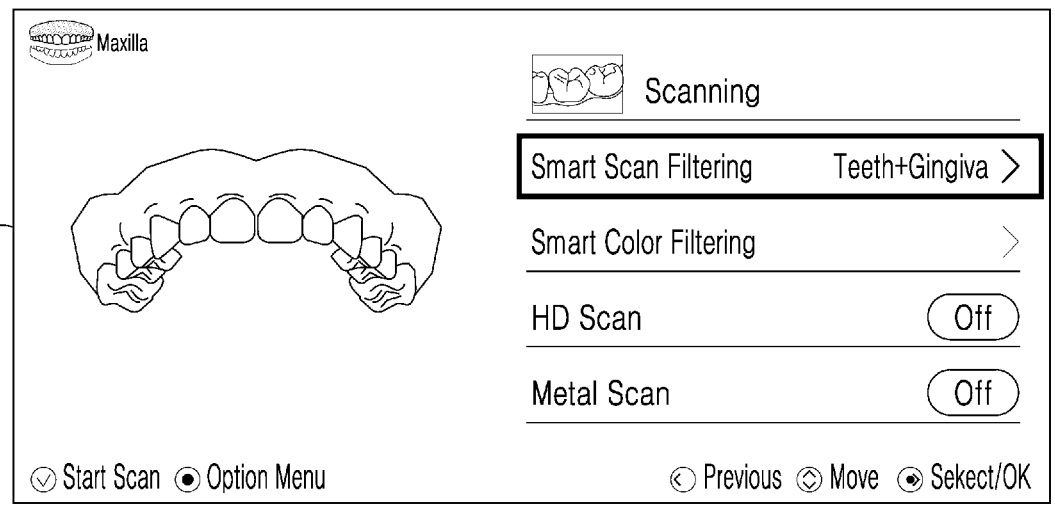
Figure 11C:
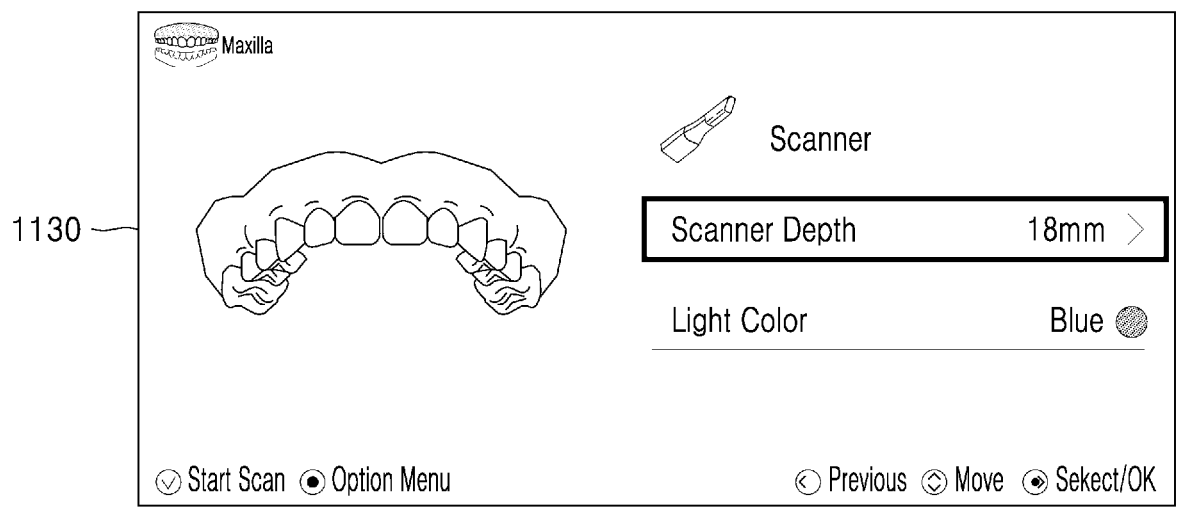

FIGS. 11A to 11C are diagrams illustrating an option setting information screen output by a data processing device, according to an embodiment.

In an embodiment, in response to the user selecting the option setting information 1015 on the screen 1010 through which the control settings shown in FIG. 10 may be accessed, the data processing device may output an option setting information screen 1110 shown in FIG. 11A.

In an embodiment, the option setting information screen 1110 is one of the remote control mode screens and may include items for setting options. Items for setting options may be included in the option setting information screen 1110 in the form of images such as large fonts or icons. Accordingly, the user may view the option setting information screen 1110 output on the screen of the data processing device, even from a place far away from the data processing device, and easily select a desired item by using a scanner.

In an embodiment, the items included in the option setting information screen 1110 may include at least one of a scan option, a scanner option, a data option, and other jog options.

In an embodiment, the option setting information screen 1110 may further include, on a portion thereof, three-dimensional scan data obtained based on raw data obtained by performing a scan operation via a scanner, but is not limited thereto.

A user may move to a desired item or select a desired item among items included in the option setting information screen 1110 by using the four direction keys and the middle key of the control button provided in the scanner.

FIG. 11B is a diagram illustrating a scan option setting information screen 1120 output when a scan option item is selected from among items included in the option setting information screen 1110.

The scan option setting information screen 1120 may include items for setting various options related to scanning. For example, the scan option setting information screen 1120 may include items, such as smart scan filtering, smart color filtering, high definition (HD) scan, and metal scan. However, the items included in the scan option setting information screen 1120 are just examples, and other items other than the above items may be further included in the scan option setting information screen 1120 or some of the above items may be excluded.

In an embodiment, the smart scan filtering item may be an item for automatically deleting unnecessary soft tissue during scanning. When the user sets the smart scan filtering item to be applied, the data processing device may automatically remove the soft tissue while performing the scan operation.

In an embodiment, the smart color filtering item may be an item for filtering a certain color during scanning. When the user sets the smart color filtering item to be applied, the data processing device may filter and remove a certain color while performing a scan operation.

In an embodiment, the HD scan item may be an item for collecting HD scan data for the whole or a certain area. When the user sets the HD scan item to be applied, the data processing device may collect and output scan data at high definition.

In an embodiment, the metal scan item may be an item for automatically detecting and processing a metal surface. When the user sets the metal scan item to be applied, the data processing device may detect and process the metal surface.

FIG. 11C is a diagram illustrating a scanner option setting information screen 1130 output when a scanner option item is selected from among items included in the option setting information screen 1110.

The scanner option setting information screen 1130 may include items for setting various options related to a scanner. For example, the scanner option setting information screen 1130 may include a scan depth item, a scan lighting item, and the like.

In the embodiment, the scan depth item is an item for setting the scan depth, and the user may set the scan depth to one of, for example, 12 mm, 15 mm, 18 mm, and 21 mm.

In an embodiment, the scan lighting item may be an item for changing the lighting color of the scanner. A user may set a scan lighting item to one of blue light and white light according to an object.

Although not shown in FIGS. 11A-11C, in an embodiment, when a user selects a data option item among items included in the option setting information screen 1110, the data processing device may output a screen including various options related to data processing, for example, data texture, display mode, data deletion, scan data alignment and noise deletion, and other multi-occlusion related items.

In an embodiment, when the user selects a jog option item among items included in the option setting information screen 1110, the data processing device may output a screen including items for changing the sensitivity of data control or the resolution of a remote control mode screen.

Figure 12:
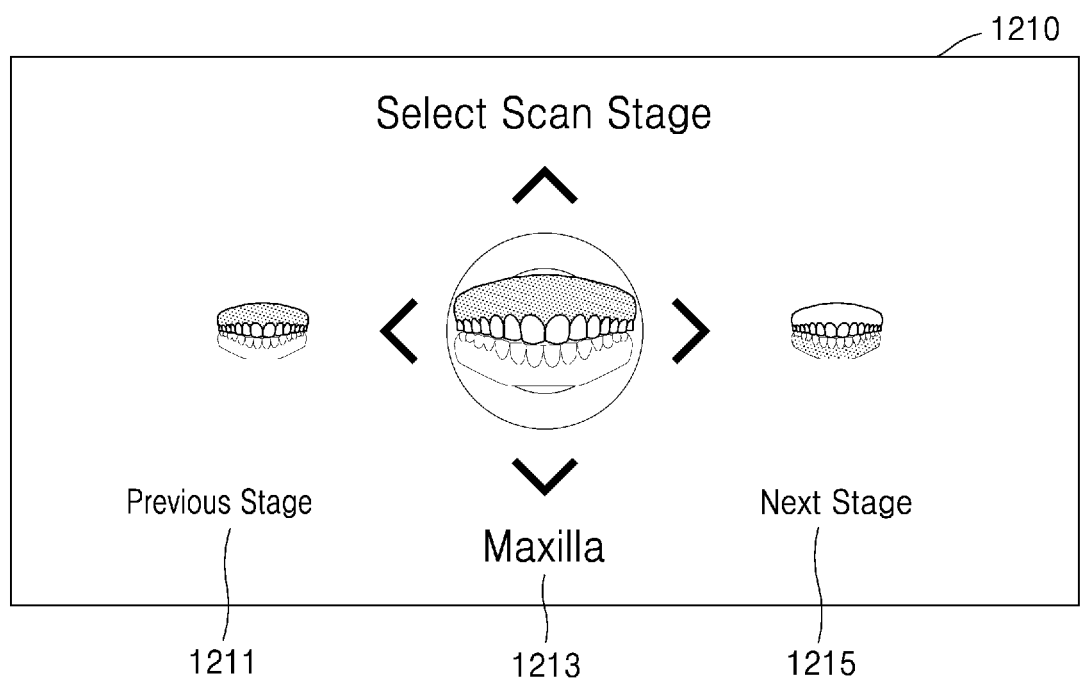
FIG. 12 is a diagram illustrating that a data processing device outputs a remote scan operation selection screen, according to an embodiment.

FIG. 12 is a diagram illustrating that a data processing device outputs a remote scan operation selection screen, according to an embodiment.

In an embodiment, the remote scan operation selection screen may refer to a screen for selecting and/or changing a scan mode.

In an embodiment, the scan mode is information for identifying an object to be scanned by the scanner, and may be one of an upper jaw scan mode, a lower jaw scan mode, and an occlusion scan mode.

In an embodiment, the user may change the scan mode while the data processing device is operating in a remote control mode. For example, the user may change the scan mode by long pressing a scan button provided in the scanner.

In an embodiment, the data processing device may output a remote scan operation selection screen 1210 in response to a long press of the scan button by the user.

In an embodiment, the remote scan operation selection screen 1210 may include at least one of a previous scan mode 1211, a current scan mode 1213, and a next scan mode 1215.

For example, when the user wants to scan the lower jaw next after scanning the upper jaw, the user may long press the scan button to output the remote scan operation selection screen 1210. The user may view the remote scan operation selection screen 1210 and check the current scan operation, or may change the scan mode to the lower jaw scan mode by inputting/pressing the four direction keys and the middle key of the control button provided in the scanner.

In an embodiment, in response to receiving a control signal from the user to change the scan operation while outputting the remote scan operation selection screen 1210, the data processing device may complete a scan operation according to the current scan mode, for example, the upper jaw scan mode, and perform post-processing on the scan data obtained in the current scan mode, and then may generate scan data for the lower jaw based on raw data received through the scanner.

Therefore, according to an embodiment, when a user ends a scan in a certain scan mode while performing the scan in the certain scan mode and wants to perform a scan according to a scan mode of a next operation, a user may easily change a scan mode by using a scan button and a control button provided in the scanner.

Figure 13:
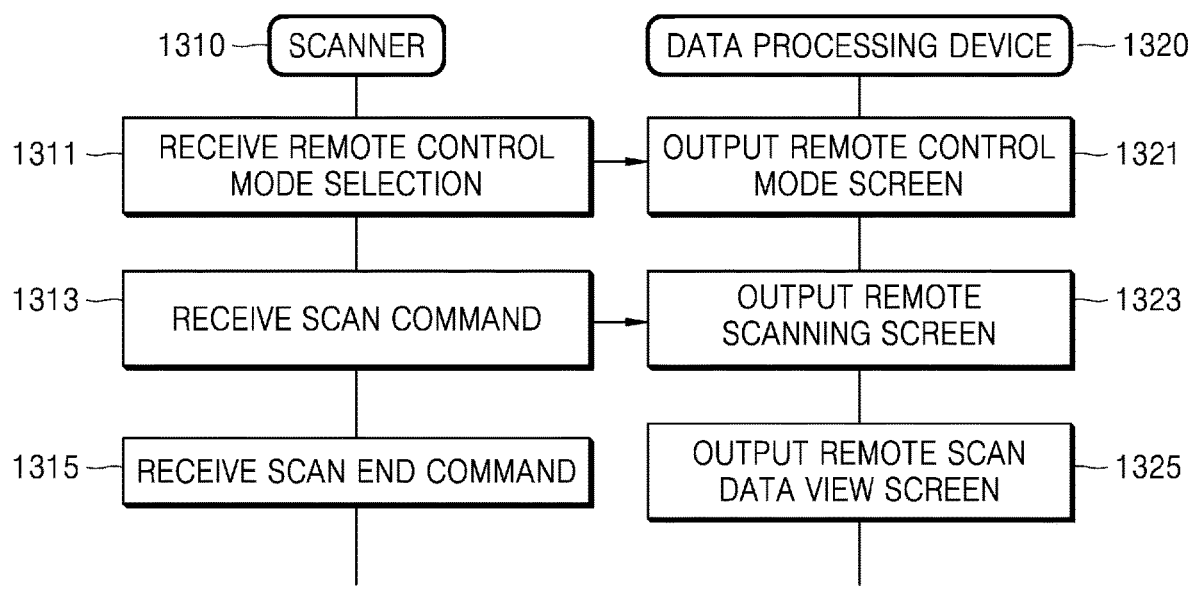
FIG. 13 is a flowchart illustrating a method of operating a data processing device in a remote control mode under the control of a scanner, according to an embodiment.

FIG. 13 is a flowchart illustrating a method of operating a data processing device in a remote control mode under the control of a scanner, according to an embodiment.

In an embodiment, a scanner 1310 may receive a remote control mode selection from a user (Operation 1311). For example, while operating in a standby mode, the scanner 1310 may receive an input for selecting a control button once from the user. The scanner 1310 may transmit a control signal including a command corresponding to a user input to a control button to a data processing device 1320.

In an embodiment, the data processing device 1320 may operate in a remote control mode based on a control signal received from the scanner 1310. In an embodiment, the data processing device 1320 may output a remote control mode screen while operating in the remote control mode (Operation 1321). In an embodiment, the remote control mode screen is a screen that may be controlled using the scanner 1310, and may refer to a screen different from a basic mode screen, which is generally output by the data processing device 1320, in at least one of a coordinate system, an output data type, and an output data size.

In an embodiment, the scanner 1310 may receive a scan command from the user while the data processing device 1320 operates in the remote control mode (Operation 1313). For example, the scanner 1310 may receive a user input to a scan button from the user. The scanner 1310 may perform a scan operation in response to a selection of the scan button by the user. Also, the scanner 1310 may transmit a control signal corresponding to a user input to the scan button to the data processing device 1320.

In an embodiment, while operating in the remote control mode, the data processing device 1320 may output a remote scanning screen in response to receiving a control signal indicating that scanning is performed from the scanner 1310 (Operation 1323). In an embodiment, the remote scanning screen may be one of remote control mode screens output while the data processing device 1320 operates in the remote control mode, and may refer to a screen that outputs, in a large size, the image and three-dimensional scan data of an object obtained from the scanner 1310 operating in a scan mode so that a user may easily recognize the image and three-dimensional scan data.

A user may perform a scan operation by using the scanner 1310 while viewing a remote scanning screen output by the data processing device 1320.

When the user wants to end the scan operation while the scanner 1310 is operating in the scan mode, the user may select a scan button provided in the scanner 1310 again. The scanner 1310 may receive a scan end command from the user (Operation 1315). The scanner 1310 may terminate a scan operation and change from a scan mode to a standby mode, in response to receiving a user input to a scan button. Also, the scanner 1310 may transmit a control signal corresponding to a user input to the scan button to the data processing device 1320.

In an embodiment, the data processing device 1320 may output a remote scan data view screen based on the control signal received from the scanner 1310 (Operation 1325). In an embodiment, the remote scan data view screen may be one of remote control mode screens output while the data processing device 1320 operates in the remote control mode, and may be a screen output to provide larger and more detailed three-dimensional scan data to the user while the scanner 1310 operates in a standby mode.

Figure 14:
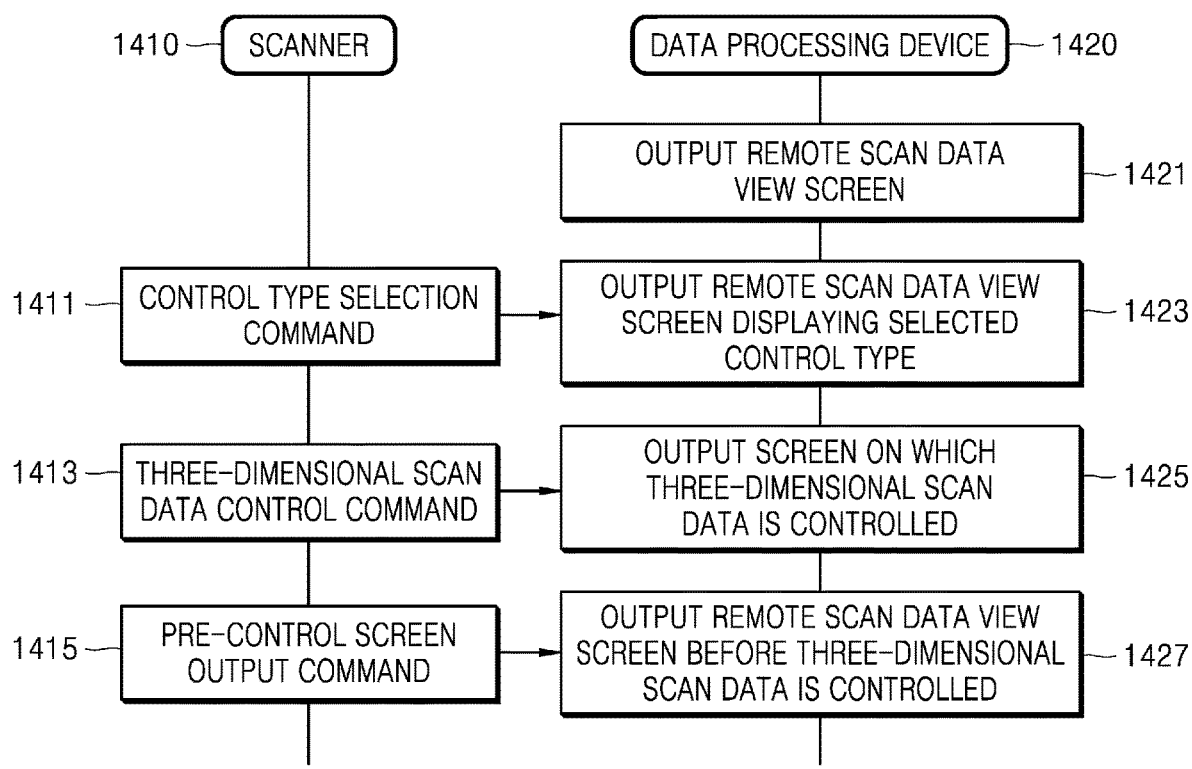
FIG. 14 is a flowchart illustrating a method of outputting a remote scan data view screen via a data processing device under the control of a scanner, according to an embodiment.

FIG. 14 is a flowchart illustrating a method of outputting a remote scan data view screen via a data processing device under the control of a scanner, according to an embodiment.

Referring to FIG. 14, while operating in the remote control mode, the data processing device 1420 may output a remote scan data view screen in response to the change of the scanner 1410 from the scan mode to the standby mode (Operation 1421). In an embodiment, the remote scan data view screen may include three-dimensional scan data in a large size in the center of the screen without a live view image.

In an embodiment, the user may select a control type by using the scanner 1410 in response to the data processing device 1420 outputting the remote scan data view screen (Operation 1411). The control type may refer to a method of controlling three-dimensional scan data included in the remote scan data view screen. The control type may include at least one of the movement, rotation, and size change (e.g., enlargement or reduction) of the three-dimensional scan data. The user may select a method of controlling the three-dimensional scan data included in the remote scan data view screen by inputting a middle key of the control button provided in the scanner 1410.

In an embodiment, the data processing device 1420 may change the control type when receiving a control signal corresponding to the control button from the scanner 1410 while outputting a remote scan data view screen. The control type may be included in and displayed on the remote scan data view screen. The user may press the control button provided in the scanner 1410 until a desired control type is displayed on the remote scan data view screen.

In an embodiment, the data processing device 1420 may output a remote scan data view screen displaying the selected control type (Operation 1423).

In an embodiment, the user may give a three-dimensional scan data control command to the scanner 1410 by inputting/pressing four direction keys of the control button provided in the scanner 1410 (Operation 1413). The scanner 1410 may transmit a control signal corresponding to the three-dimensional scan data control command to the data processing device 1420, and thus, the data processing device 1420 may output a screen on which the three-dimensional scan data is controlled according to the control type and the four-directional key input (Operation 1425).

In an embodiment, the user may issue a command to output a pre-control screen by selecting/inputting/pressing a middle key of the control button included in the scanner 1410 a certain number of times (Operation 1415). When receiving a control signal from the scanner 1410 to output a pre-control screen, the data processing device 1420 may output a remote scan data view screen before the three-dimensional scan data is controlled (Operation 1427).

Figure 15:
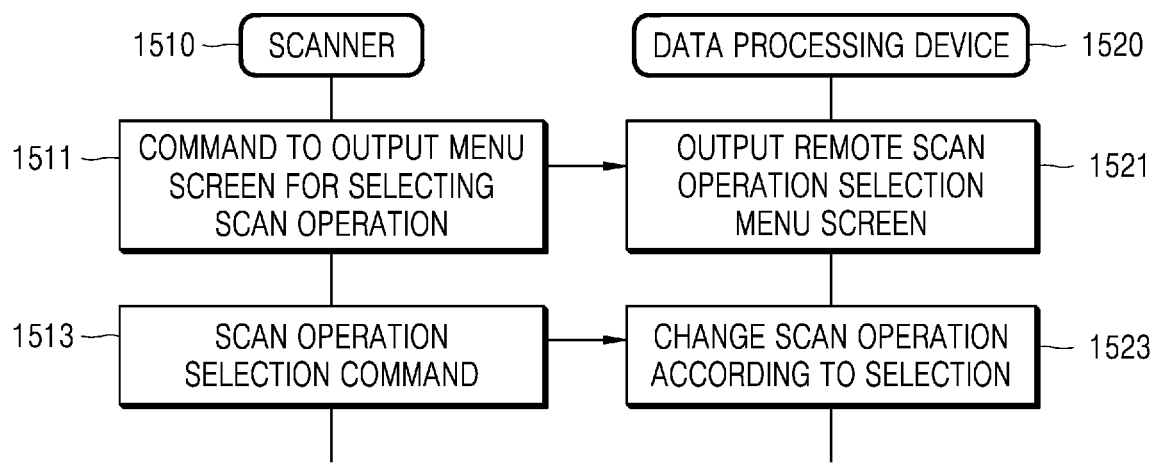
FIG. 15 is a flowchart illustrating a method of changing a scan operation in a remote control mode via a data processing device under the control of a scanner, according to an embodiment.

FIG. 15 is a flowchart illustrating a method of changing a scan operation in a remote control mode via a data processing device under the control of a scanner, according to an embodiment.

Referring to FIG. 15, the user may change a scan mode by using a scan button provided in a scanner 1510. For example, when the user long presses the scan button, the scanner 1510 may issue a command to output a menu screen for selecting a scan operation according to a user input (Operation 1511). In an embodiment, a data processing device 1520 may output a remote scan operation selection screen according to a control signal from the scanner 1510 (Operation 1521).

The user may input the four-directional key and the middle key of the control button provided in the scanner 1510 in response to the data processing device 1520 outputting the remote scan operation selection screen. The scanner 1510 may generate a control signal according to the user input and transmit the control signal to the data processing device 1520 to issue a scan operation selection command (Operation 1513).

In an embodiment, the data processing device 1520 may complete a scan according to the current scan mode and change the scan operation to a scan mode selected by the user, in response to receiving a command to change the scan operation from the scanner 1510 (Operation 1523).

Figure 16:
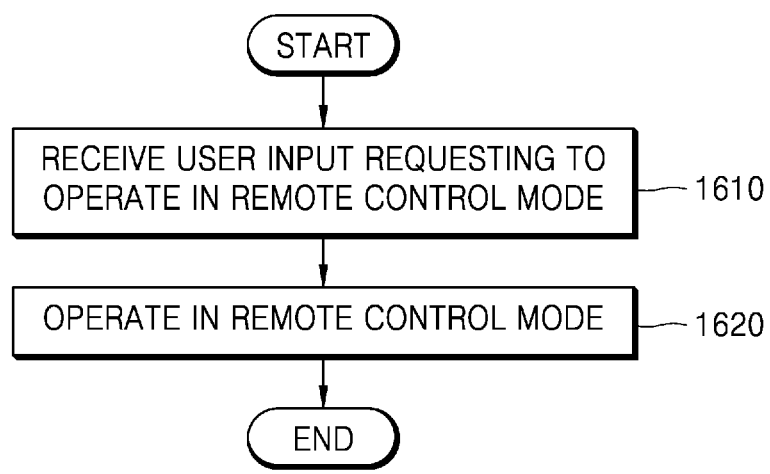
FIG. 16 is a flowchart illustrating that a data processing device operates in a remote control mode under the control of a scanner, according to an embodiment.

FIG. 16 is a flowchart illustrating that a data processing device operates in a remote control mode under the control of a scanner, according to an embodiment.

Referring to FIG. 16, the data processing device may receive a user input requesting to operate in a remote control mode (Operation 1610).

For example, while the scanner operates in a standby mode, a control signal corresponding to a user input to a control button provided in the scanner may be received. The control signal corresponding to a user input to the control button provided in the scanner may include a remote control signal. The remote control signal may include a signal for changing the display of three-dimensional scan data. Also, the remote control signal may include a signal instructing to output a remote control mode screen. The data processing device may operate in a remote control mode according to a control signal.

Alternatively, the data processing device may be directly selected to operate in the remote control mode from the user through a user input unit provided in the data processing device, for example, a mouse or a keyboard.

The data processing device may operate in the remote control mode in response to receiving a user input requesting to operate in the remote control mode (Operation 1620).

In an embodiment, the data processing device may output a remote control mode screen while operating in the remote control mode. The user may remotely and easily control the data processing device by viewing the remote control mode screen output on the data processing device at a location away from the data processing device and providing a user input through a scanner.

A data processing method according to an embodiment of the present disclosure may be implemented in the form of a program command to be executed through various computer devices and recorded on a computer-readable medium. In addition, the embodiment of the present disclosure may include a computer-readable storage medium having recorded thereon one or more programs including at least one instruction to execute a data processing method.

In addition, the data processing method according to the embodiment of the disclosure described above may be implemented as a computer program product including a computer-readable recording medium having recorded thereon a program for implementing a data processing method, the data processing method including displaying three-dimensional scan data and changing the display of the three-dimensional scan data in response to a remote control signal received from a scanner, wherein the remote control signal includes a signal for controlling a virtual camera that obtains an image of the three-dimensional scan data.

The computer-readable storage medium may include program commands, data files, and data structures either alone or in combination. Examples of the computer-readable storage medium may include magnetic media such as hard disks, floppy disks, or magnetic tapes, optical media such as CD-ROMs or DVDs, and magneto-optical media such as floptical disks, and hardware devices such ROMs, RAMs, or flash memories configured to store and execute program commands.

Here, a machine-readable storage medium may be provided in the form of a non-transitory storage medium. Here, the "non-transitory storage medium" may mean that the storage medium is a tangible device. Also, the "non-transitory storage medium" may include a buffer in which data is temporarily stored.

Although embodiments have been described above in detail, the scope of the present disclosure is not limited thereto and various modifications and improvements made by those of ordinary skill in the art by using the basic concept of the present disclosure defined in the following claims are also included in the scope of the present disclosure.

The invention claimed is:

1. A data processing method comprising:
   displaying three-dimensional scan data; and
   changing display of the three-dimensional scan data in response to a remote control signal received from a scanner,
   wherein the remote control signal includes a signal for controlling a virtual camera obtaining an image of the three-dimensional scan data,
   wherein the signal for controlling the virtual camera controls the virtual camera to operate in an opposite direction of a user input signal received through the scanner, and
   wherein the changing of the display of the three-dimensional scan data comprises:
   controlling the virtual camera to operate in the opposite direction of the user input signal received through the scanner, and
   capturing an image of the three-dimensional scan data with the virtual camera and outputting the captured image.

2. The data processing method of claim 1, wherein the remote control signal further includes a signal instructing to output a remote control mode screen.

3. The data processing method of claim 2, further comprising outputting a remote scanning screen in response to receiving a scan start signal from the scanner.

4. The data processing method of claim 3, wherein the remote scanning screen includes the three-dimensional scan data and a live view image, and the live view image is a two-dimensional image of an object obtained by the scanner.

5. The data processing method of claim 1, further comprising receiving the remote control signal from the scanner,
   wherein the receiving of the remote control signal from the scanner includes receiving, as the remote control signal, a user input signal for selecting a control button provided in the scanner.

6. The data processing method of claim 2, wherein the remote control mode screen is different from a basic mode screen in at least one of a coordinate system, an output data type, and an output data size.

7. The data processing method of claim 2, further comprising receiving a signal instructing to output a basic mode screen,
   wherein the receiving of the signal instructing to output the basic mode screen includes at least one of receiving a user input signal for selecting to output a basic mode of a menu, output on the remote control mode screen through a control button provided in the scanner, while outputting the remote control mode screen, and sensing an input signal by an input unit of a data processing device.

8. The data processing method of claim 2, further comprising:
   outputting a remote scan operation selection screen in response to receiving a user input signal by long pressing a scan button provided in the scanner from the scanner; and
   changing a scan operation according to a user input signal through a control button provided in the scanner,
   wherein the changing of the scan operation includes completing data generated in a previous scan operation.

9. The data processing method of claim 2, further comprising outputting a remote scan data view screen in response to receiving a scan end signal from the scanner.

10. The data processing method of claim 9, further comprising receiving, from the scanner, a user input signal for selecting a control type for the three-dimensional scan data included in the remote scan data view screen,
    wherein the control type for the three-dimensional scan data includes at least one of movement, rotation, and size change of the three-dimensional scan data.

11. The data processing method of claim 1, wherein the signal for controlling the virtual camera includes a selected control type and the user input signal corresponding to an input of a control button provided in the scanner.

12. A data processing device comprising:
    a display;
    a communication unit configured to transmit and receive information to and from a scanner; and
    a processor configured to execute one or more instructions,
    wherein the processor is further configured to execute the one or more instructions to:
    receive a user input signal through the scanner,
    display three-dimensional scan data through the display, and
    change the display of the three-dimensional scan data in response to a remote control signal received from the scanner, wherein the remote control signal includes a signal for controlling a virtual camera obtaining an image of the three-dimensional scan data, wherein the signal for controlling the virtual camera controls the virtual camera to operate in an opposite direction of the user input signal, and wherein the processor is further configured to:

control the virtual camera to operate in the opposite direction of the user input signal, capture an image of the three-dimensional scan data using the virtual camera, and output the captured image.

13. A scanner comprising:

a communication unit configured to transmit and receive information to and from a data processing device;

a user input unit; and a processor configured to execute one or more instructions, wherein the processor is further configured to execute the one or more instructions to:

transmit a remote control signal corresponding to a user input through the user input unit to the data processing device, and control the data processing device to change display of three-dimensional scan data, wherein the remote control signal includes a signal for controlling a virtual camera to obtain an image of the three-dimensional scan data, and wherein the signal for controlling the virtual camera controls the virtual camera to operate in an opposite direction of the user input signal received through the user input unit.

* * * * *